US012752258B2

(12) United States Patent
Garg et al.

(10) Patent No.: US 12,752,258 B2
(45) Date of Patent: Oct. 6, 2026

(54) CATALYST COMPOSITIONS AND PROCESSES FOR MAKING AND USING SAME

(71) Applicant: ExxonMobil Chemical Patents Inc., Baytown, TX (US)

(72) Inventors: Aaron R. Garg, San Francisco, CA (US); Xiaoying Bao, Houston, TX (US); Colin L. Beswick, Lebanon, NJ (US); Chuansheng Bai, Phillipsburg, NJ (US); Christian A. Diaz Urrutia, Auderghem (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 110 days.

(21) Appl. No.: 18/569,159

(22) PCT Filed: Jun. 27, 2022

(86) PCT No.: PCT/US2022/035120
§ 371 (c)(1),
(2) Date: Dec. 11, 2023

(87) PCT Pub. No.: WO2023/009259
PCT Pub. Date: Feb. 2, 2023

(65) Prior Publication Data

US 2024/0269653 A1 Aug. 15, 2024

Related U.S. Application Data

(60) Provisional application No. 63/328,987, filed on Apr. 8, 2022, provisional application No. 63/226,377, filed on Jul. 28, 2021.

(51) Int. Cl.
*B01J 23/62* (2006.01)
*B01J 21/08* (2006.01)
(Continued)

(52) U.S. Cl.
CPC ............ *B01J 23/626* (2013.01); *B01J 21/08* (2013.01); *B01J 21/16* (2013.01); *B01J 23/02* (2013.01);
(Continued)

(58) Field of Classification Search
CPC . B01J 23/626; B01J 21/08; B01J 21/16; B01J 23/02; B01J 35/32; B01J 35/38;
(Continued)

(56) References Cited

U.S. PATENT DOCUMENTS 4,179,469 A 12/1979 Imai
4,866,019 A 9/1989 van Broekhoven
(Continued)

FOREIGN PATENT DOCUMENTS

CN 104511291 A 4/2015
CN 104511292 A 4/2015
(Continued)

OTHER PUBLICATIONS

Wang et al., "Preparation of Layered Double Hydroxide Microspheres by Spray Drying." *Ind. Eng. Chem. Res.* 2008, 47, 5746-5750.
(Continued)

*Primary Examiner* — Prem C Singh
*Assistant Examiner* — Francis C Campanell
(74) *Attorney, Agent, or Firm* — Kevin Davis; WOMBLE BOND DICKINSON (US) LLP

(57) ABSTRACT

Catalyst compositions and processes for making and using same. The catalyst composition can include catalyst particles. The catalyst particles can include 0.001 wt % to 6 wt % of Pt and up to 10 wt % of a promoter that can include Sn, Cu, Au, Ag, Ga, or a combination thereof, or a mixture thereof disposed on a support. The support can include at least 0.5 wt % of a Group 2 element. All weight percent values are based on the weight of the support. The catalyst
(Continued)

particles can have a median particle size in a range from 10 µm to 500 pm. The catalyst particles can have an apparent loose bulk density in a range from 0.3 g/cm$^3$ to 2 g/cm$^3$, as measured according to ASTM D7481-18 modified with a 10, 25, or 50 mL graduated cylinder instead of a 100 or 250 mL graduated cylinder.

24 Claims, 2 Drawing Sheets

(51) Int. Cl.

| | |
|---|---|
| ***B01J 21/16*** | (2006.01) |
| ***B01J 23/02*** | (2006.01) |
| ***B01J 35/32*** | (2024.01) |
| ***B01J 35/38*** | (2024.01) |
| ***B01J 35/45*** | (2024.01) |
| ***B01J 35/73*** | (2024.01) |
| ***B01J 37/00*** | (2006.01) |
| ***B01J 37/02*** | (2006.01) |
| ***B01J 37/08*** | (2006.01) |
| ***B01J 37/10*** | (2006.01) |
| ***C07C 5/32*** | (2006.01) |

(52) U.S. Cl.

CPC ............... *B01J 35/32* (2024.01); *B01J 35/38* (2024.01); *B01J 35/45* (2024.01); *B01J 35/73* (2024.01); *B01J 37/0009* (2013.01); *B01J 37/0221* (2013.01); *B01J 37/0236* (2013.01); *B01J 37/088* (2013.01); *B01J 37/10* (2013.01); *C07C 5/325* (2013.01); *C07C 2523/14* (2013.01); *C07C 2523/42* (2013.01); *C07C 2523/66* (2013.01); *C07C 2523/89* (2013.01)

(58) Field of Classification Search

CPC ........ B01J 35/45; B01J 35/73; B01J 37/0009; B01J 37/0221; B01J 37/0236; B01J 37/088; B01J 37/10; B01J 37/0045; B01J 37/0201; B01J 35/40; C07C 5/325; C07C 2523/14; C07C 2523/42; C07C 2523/66; C07C 2523/89; Y02P 20/52; C10G 11/02

USPC .......................................................... 585/660

See application file for complete search history.

(56) References Cited

U.S. PATENT DOCUMENTS

| | | | | |
|---|---|---|---|---|
| 5,912,394 | A | 6/1999 | Rotgerink et al. | |
| 6,028,023 | A | 2/2000 | Vierheilig | |
| 6,300,268 | B1 | 10/2001 | Lapidus et al. | |
| 6,589,902 | B1 | 7/2003 | Stamires et al. | |
| 6,967,182 | B1 * | 11/2005 | Olsbye | C07C 5/02 502/80 |
| 7,235,706 | B2 | 6/2007 | Iezzi et al. | |
| 7,361,264 | B2 | 4/2008 | Vierheilig | |
| 7,417,005 | B2 | 8/2008 | Vierheilig | |
| 10,682,628 | B2 | 6/2020 | Serban et al. | |
| 10,682,631 | B2 | 6/2020 | Amakawa et al. | |
| 11,760,703 | B2 | 9/2023 | Bao et al. | |
| 11,773,336 | B2 | 10/2023 | Bao et al. | |
| 11,859,136 | B2 | 1/2024 | Bao | |
| 2002/0098976 | A1 | 7/2002 | Rytter et al. | |
| 2002/0198428 | A1 | 12/2002 | Iezzi et al. | |
| 2004/0029729 | A1 | 2/2004 | Rytter et al. | |
| 2004/0214904 | A1 | 10/2004 | Singleton et al. | |
| 2005/0000396 | A1 | 1/2005 | Dyson et al. | |
| 2012/0067778 | A1 | 3/2012 | Sanchez Valente et al. | |
| 2017/0354955 | A1 * | 12/2017 | Hossain | B01J 35/612 |
| 2019/0015819 | A1 * | 1/2019 | Avenier | B01J 27/1856 |
| 2019/0126256 | A1 * | 5/2019 | Serban | B01J 35/67 |
| 2021/0031176 | A1 | 2/2021 | Suriye et al. | |
| 2022/0266224 | A1 * | 8/2022 | Dong | B01J 37/0009 |
| 2022/0275289 | A1 | 9/2022 | Bao et al. | |

FOREIGN PATENT DOCUMENTS

| | | | |
|---|---|---|---|
| WO | WO2008/083563 | | 7/2008 |
| WO | 2021/225747 | A1 | 11/2021 |
| WO | 2023/009259 | A1 | 2/2023 |

OTHER PUBLICATIONS

Chubar et al., "Applications versus properties of Mg—Al layered double hydroxides provided by their syntheses methods: Alkoxide and alkoxide-free sol-gel syntheses and hydrothermal precipitation" Chem. Eng. J. 2013, 234, 284-299.

* cited by examiner

CATALYST COMPOSITIONS AND PROCESSES FOR MAKING AND USING SAME

CROSS-REFERENCE TO RELATED APPLICATIONS

This application is a US national phase application of PCT Application Serial No. PCT/US2022/035120 having a filing date of Jun. 27, 2022, which claims priority to and the benefit of U.S. Provisional Application No. 63/226,377 having a filing date of Jul. 28, 2021, and U.S. Provisional Application No. 63/328,987 having a filing date of Apr. 8, 2022, the disclosures of all of which are incorporated herein by reference in their entireties.

FIELD

This disclosure relates to catalyst compositions and processes for making and using same.

BACKGROUND

Catalytic reforming or dehydrogenation, dehydroaromatization, and/or dehydrocyclization of alkane and/or alkyl aromatic hydrocarbons are industrially important chemical conversion processes that are endothermic and equilibrium-limited. The reforming or dehydrogenation dehydroaromatization, and/or dehydrocyclization of alkanes, e.g., $C_1$-$C_{12}$ alkanes, and/or alkyl aromatics, e.g., ethylbenzene, can be done through a variety of different powdered catalysts such as the Pt-based, Ni-based, Pd-based, Ru-based, Re-based, Cr-based, Ga-based, V-based, Zr-based, In-based, W-based, Mo-based, Zn-based, and Fe-based systems.

For a powdered catalyst to be used in a commercial fluid bed process, the powdered catalyst must be formed into a fluid bed catalyst composition that is in the form of particles and either separately or simultaneously, the active metal, e.g., Pt, needs to be added thereto. Several issues can arise during the making of the fluid bed catalyst particles. For example, the formed fluid bed catalyst particles can have an undesirable particle size, an undesirable bulk density, and/or an undesirable average sphericity, which could negatively impact the fluidization. The process used to make the fluid bed catalyst particles can also result in a decrease in catalyst performance as compared to the powdered catalyst, and the formed fluid bed catalyst particles can have an insufficient resistance to attrition causing the fluid bed catalyst particles to excessively break up when used in the commercial fluid bed process.

There is a need, therefore, for improved catalyst compositions and processes for making and using same. This disclosure satisfies this and other needs.

SUMMARY

Catalyst compositions and processes for making and using same are provided. In some embodiments, the catalyst composition can include catalyst particles. The catalyst particles can include 0.001 wt % to 6 wt % of Pt and up to 10 wt % of a promoter that can include Sn, Cu, Au, Ag, Ga, or a combination thereof, or a mixture thereof disposed on a support. The support can include at least 0.5 wt % of a Group 2 element, where all weight percent values are based on the weight of the support. The catalyst particles can have a median particle size in a range from 10 μm to 500 μm. The catalyst particles can have an apparent loose bulk density in a range from 0.3 g/cm$^3$ to 2 g/cm$^3$, as measured according to ASTM D7481-18 modified with a 10, 25, or 50 mL graduated cylinder instead of a 100 or 250 mL graduated cylinder.

In some embodiments, the process for making a catalyst composition can include: (I) preparing a slurry or gel that can include a compound containing a Group 2 element and a liquid medium. The process can also include (II) spray drying the slurry or the gel to produce spray dried particles that include the Group 2 element. The process can also include (III) calcining the spray dried particles under an oxidative atmosphere to produce calcined support particles comprising the Group 2 element. The process can also include at least one of (i), (ii), and (iii): (i) Pt can be present in the slurry or the gel in the form of a Pt-containing compound and the catalyst composition can include catalyst particles that include the calcined support particles having Pt disposed thereon, (ii) Pt can be deposited on the spray dried particles by contacting the spray dried particles with a Pt-containing compound to produce Pt-containing spray dried particles and the catalyst composition can include catalyst particles that include the calcined support particles having Pt disposed thereon, and (iii) Pt can be deposited on the calcined support particles by contacting the calcined support particles with a Pt-containing compound to produce Pt-containing calcined support particles and the process can further include (IV) calcining the Pt-containing calcined support particles to produce re-calcined support particles having Pt disposed thereon, where the catalyst composition includes the re-calcined support particles. The process can also include at least one of (iv), (v), and (vi): (iv) a compound that includes a promoter element can be present in the slurry or the gel and the catalyst composition can include catalyst particles that include the calcined support particles having the promoter element disposed thereon, (v) a compound that includes a promoter element can be deposited on the spray dried particles to produce promoter-containing spray dried particles and the catalyst composition can include catalyst particles that include the calcined support particles having the promoter element disposed thereon, and (vi) a compound that includes a promoter element can be deposited on the calcined support particles to produce promoter-containing calcined support particles and the process can further include (V) calcining the promoter-containing calcined support particles to produce re-calcined support particles having the promoter element disposed thereon, where the catalyst composition includes the re-calcined support particles. The promoter element can include Sn, Cu, Au, Ag, Ga, or a combination thereof, or a mixture thereof. The catalyst particles can include from 0.001 wt % to 6 wt % of the Pt based on the weight of the calcined support particles or the re-calcined support particles. The catalyst particles can include at least 0.5 wt % of the Group 2 element based on the weight of the calcined support particles or the re-calcined support particles. The catalyst particles can have a median particle size in a range of from 10 μm to 500 μm. The catalyst particles can have an apparent loose bulk density in a range of from 0.3 g/cm$^3$ to 2 g/cm$^3$ as measured according to ASTM D7481-18 modified with a 10, 25, or 50 mL graduated cylinder instead of a 100 or 250 mL graduated cylinder.

In some embodiments, a process for upgrading a hydrocarbon can include (I) contacting a hydrocarbon-containing feed with catalyst particles that include Pt disposed on a support to effect one or more of dehydrogenation, dehydroaromatization, and dehydrocyclization of at least a portion of the hydrocarbon-containing feed to produce a coked catalyst and an effluent that can include one or more upgraded hydrocarbons and molecular hydrogen. The hydrocarbon-containing feed can include one or more of $C_2$-$C_{16}$ linear or branched alkanes, or one or more of $C_4$-$C_{16}$ cyclic alkanes, or one or more $C_8$-$C_{16}$ alkyl aromatics, or a mixture thereof. The hydrocarbon-containing feed and catalyst can be contacted at a temperature in a range of from 300° C. to 900° C., for a time period of ≤3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. The support can include at least 0.5 wt % of a Group 2 element. The catalyst can include from 0.001 wt % to 6 wt % of the Pt based on the weight of the support. The catalyst particles can have a median particle size in a range of from 10 μm to 500 μm. The catalyst particles can have an apparent loose bulk density in a range of from 0.3 g/cm$^3$ to 2 g/cm$^3$ as measured according to ASTM D7481-18 modified with a 10, 25, or 50 mL graduated cylinder instead of a 100 or 250 mL graduated cylinder. The one or more upgraded hydrocarbons can include at least one of a dehydrogenated hydrocarbon, a dehydroaromatized hydrocarbon, and a dehydrocyclized hydrocarbon.

DETAILED DESCRIPTION

Figure 1:
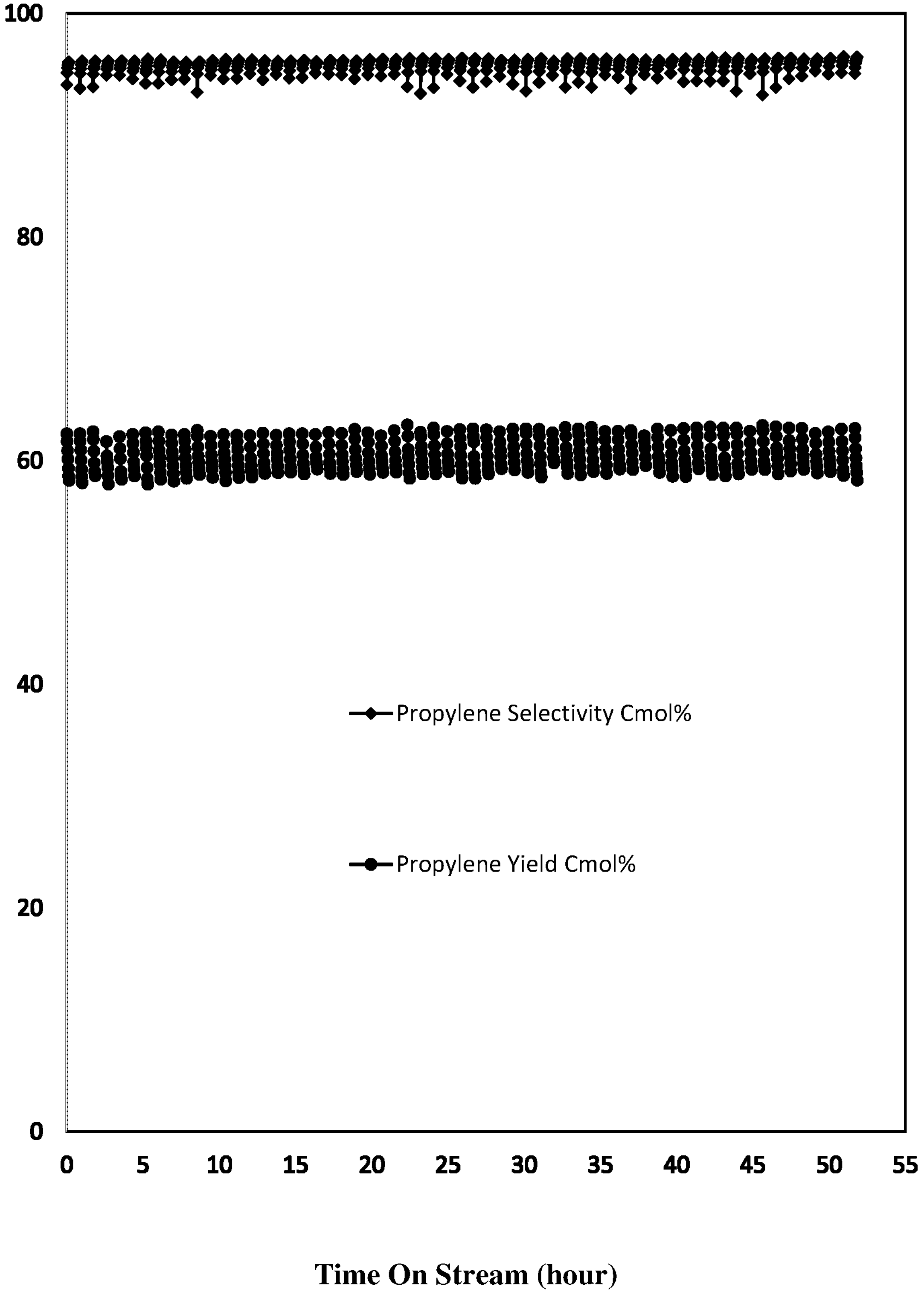
FIG. 1 shows a catalyst composition 2 was stable for over 60 cycles for propane dehydrogenation.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, 16$^{th}$ Ed., John Wiley & Sons, Inc., (2016), Appendix V. For example, a Group 2 element includes Mg, a Group 8 element includes Fe, a Group 9 element includes Co, a Group 10 element includes Ni, and a Group 13 element includes Al. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "alkane" means a saturated hydrocarbon. The term "cyclic alkane" means a saturated hydrocarbon comprising a cyclic carbon ring in the molecular structure thereof. An alkane can be linear, branched, or cyclic.

The term "aromatic" is to be understood in accordance with its art-recognized scope, which includes alkyl substituted and unsubstituted mono- and polynuclear compounds.

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The term "mixed metal oxide" refers to a composition that includes oxygen atoms and at least two different metal atoms that are mixed on an atomic scale. For example, a "mixed Mg/Al metal oxide" has O, Mg, and Al atoms mixed on an atomic scale and is substantially the same as or identical to a composition obtained by calcining an Mg/Al hydrotalcite that has the general chemical formula $$\left[Mg_{(1-x)}Al_x(OH)_2\right]\left(A^{n-}_{\frac{x}{n}}\right)\cdot mH_2O\Big],$$

where A is a counter anion of a negative charge n, x is in a range of from >0 to <1, and m is ≥0. A material consisting of nm sized MgO particles and nm sized $Al_2O_3$ particles mixed together is not a mixed metal oxide because the Mg and Al atoms are not mixed on an atomic scale but are instead mixed on a nm scale.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. In another example, when the specified reactant is propane, if one mole of propane convers to one mole of methane and one mole of ethylene, the selectivity to methane is 33.3% and the selectivity to ethylene is 66.7%. Yield (carbon mole basis) is conversion times selectivity.

In this disclosure, "A, B, . . . or a combination thereof" means "A, B, . . . or any combination of any two or more of A, B, . . . " "A, B, . . . , or a mixture thereof" means "A, B, . . . , or any mixture of any two or more of A, B, . . . ."

Catalyst Composition

The catalyst composition can be or can include, but is not limited to, catalyst particles. The catalyst particles can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of Pt disposed on a support, based on the weight of the support. In some embodiments, the catalyst particles can include ≤5.5 wt %, ≤4.5 wt %, ≤3.5 wt %, ≤2.5 wt %, ≤1.5 wt %, ≤1 wt %, ≤0.9 wt %, ≤0.8 wt %, ≤0.7 wt %, ≤0.6 wt %, ≤0.5 wt %, ≤0.4 wt %, ≤0.3 wt %, ≤0.2 wt %, ≤0.15 wt %, ≤0.1 wt %, ≤0.09 wt %, ≤0.08 wt %, ≤0.07 wt %, ≤0.06 wt %, ≤0.05 wt %, ≤0.04 wt %, ≤0.03 wt %, ≤0.02 wt %, ≤0.01 wt %, ≤0.009 wt %, ≤0.008 wt %, ≤0.007 wt %, ≤0.006 wt %, ≤0.005 wt %, ≤0.004 wt %, ≤0.003 wt %, or ≤0.002 wt % of Pt disposed on the support, based on the weight of the support. In some embodiments, the catalyst particles can include >0.001, >0.003 wt %, >0.005 wt %, >0.007, >0.009 wt %, >0.01 wt %, >0.02 wt %, >0.04 wt %, >0.06 wt %, >0.08 wt %, >0.1 wt %, >0.13 wt %, >0.15 wt %, >0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of Pt disposed on the support, based on the weight of the support. In some embodiments, the catalyst particles can optionally also include Ni, Pd, or a combination thereof, or a mixture thereof. If Ni, Pd, or a combination thereof, or a mixture thereof is also disposed on the support the catalyst particles can include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a combined amount of Pt and any Ni and/or any Pd disposed on the support, based on the weight of the support. In some embodiments, an active component of the catalyst particles that can be capable of effecting one or more of reforming or dehydrogenation, dehydroaromatization, and dehydrocyclization of a hydrocarbon-containing feed can include the Pt or the Pt and Ni and/or Pd.

The catalyst particles can include a promoter in an amount of up to 10 wt % disposed on the support, based on the weight of the support. The promoter can be or can include, but is not limited to, Sn, Cu, Au, Ag, Ga, or a combination thereof, or a mixture thereof. In some embodiments, the promoter can be associated with the Pt and/or, if present, the Ni and/or Pd. For example, the promoter and the Pt disposed on the support can form Pt-promoter clusters that can be dispersed on the support. The promoter can improve the selectivity/activity/longevity of the catalyst particles for a given upgraded hydrocarbon. In some embodiments, the promoter can improve the propylene selectivity of the catalyst particles when the hydrocarbon-containing feed includes propane. The catalyst particles can include the promoter in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 3 wt %, 5 wt %, 7 wt %, or 10 wt %, based on the weight of the support.

In some embodiments, the catalyst particles can optionally include one or more alkali metal elements in an amount of up to 5 wt % disposed on the support, based on the weight of the support. The alkali metal element, if present, can be or can include, but is not limited to, Li, Na, K, Rb, Cs, or a combination thereof, or a mixture thereof. In at least some embodiments, the alkali metal element ca be or can include K and/or Cs. In some embodiments, the alkali metal element, if present, can improve the selectivity of the catalyst particles for a given upgraded hydrocarbon. The catalyst particles can include the alkali metal element in an amount of 0.01 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, or 5 wt %, based on the weight of the support.

The support can be or can include, but is not limited to, one or more Group 2 elements, or a combination thereof, or a mixture thereof. In some embodiments, the Group 2 element can be present in its elemental form. In other embodiments, the Group 2 element can be present in the form of a compound. For example, the Group 2 element can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element can be present in different forms. For example, a first compound can be an oxide and a second compound can be an aluminate where the first compound and the second compound include the same or different Group 2 element, with respect to one another.

The support can include ≥0.5 wt %, ≥1 wt %, ≥2 wt %, ≥3 wt %, ≥4 wt %, ≥5 wt %, ≥6 wt %, ≥7 wt %, ≥8 wt %, ≥9 wt %, ≥10 wt %, ≥11 wt %, ≥12 wt %, ≥13 wt %, ≥14 wt %, ≥15 wt %, ≥16 wt %, ≥17 wt %, ≥18 wt %, ≥19 wt %, ≥20 wt %, ≥21 wt %, ≥22 wt %, ≥23 wt %, ≥24 wt %, ≥25 wt %, ≥26 wt %, ≥27 wt %, ≥28 wt %, ≥29 wt %, ≥30 wt %, ≥35 wt %, ≥40 wt %, ≥45 wt %, ≥50 wt %, ≥55 wt %, ≥60 wt %, ≥65 wt %, ≥70 wt %, ≥75 wt %, ≥80 wt %, ≥85 wt %, or ≥90 wt % of the Group 2 element, based on the weight of the support. In some embodiments, the support can include the Group 2 element in a range of from 0.5 wt %, 1 wt %, 2 wt %, 2.5 wt %, 3 wt %, 5 wt %, 7 wt %, 10 wt %, 11 wt %, 13 wt %, 15 wt %, 17 wt %, 19 wt %, 21 wt %, 23 wt %, or 25 wt % to 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, or 92.34 wt % based on the weight of the support. In some embodiments, a molar ratio of the Group 2 element to the Pt or the Pt and any Ni and/or Pd present can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500, 000, 600,000, 700,000, 800,000, or 900,000.

In some embodiments, the support can include the Group 2 element and Al and can be in the form of a mixed Group 2 element/Al metal oxide that has O, Mg, and Al atoms mixed on an atomic scale. In some embodiments the support can be or can include the Group 2 element and Al in the form of an oxide or one or more oxides of the Group 2 element and $Al_2O_3$ that can be mixed on a nm scale. In some embodiments, the support can be or can include an oxide of the Group 2 element, e.g., MgO, and $Al_2O_3$ mixed on a nm scale.

In some embodiments, the support can be or can include a first quantity of the Group 2 element and Al in the form of a mixed Group 2 element/Al metal oxide and a second quantity of the Group 2 element in the form of an oxide of the Group 2 element. In such embodiment, the mixed Group 2 element/Al metal oxide and the oxide of the Group 2 element can be mixed on the nm scale and the Group 2 element and Al in the mixed Group 2 element/Al metal oxide can be mixed on the atomic scale.

In other embodiments, the support can be or can include a first quantity of the Group 2 element and a first quantity of Al in the form of a mixed Group 2 element/Al metal oxide, a second quantity of the Group 2 element in the form of an oxide of the Group 2 element, and a second quantity of Al in the form of $Al_2O_3$. In such embodiment, the mixed Group 2 element/Al metal oxide, the oxide of the Group 2 element, and the $Al_2O_3$ can be mixed on a nm scale and the Group 2 element and Al in the mixed Group 2 element/Al metal oxide can be mixed on the atomic scale.

In some embodiments, when the support includes the Group 2 element and Al, a weight ratio of the Group 2 element to the Al in the support can be in a range from 0.001, 0.005, 0.01, 0.05, 0.1, 0.15, 0.2, 0.3, 0.5, 0.7, or 1 to 3, 6, 12.5, 25, 50, 75, 100, 200, 300, 400, 500, 600, 700, 800, 900, or 1,000. In some embodiments, when the support includes Al, the support can include Al in a range from 0.5 wt %, 1 wt %, 1.5 wt %, 2 wt %, 2.1 wt %, 2.3 wt %, 2.5 wt %, 2.7 wt %, 3 wt %, 4 wt %, 5 wt %, 6 wt %, 7 wt %, 8 wt %, 9 wt %, 10 wt %, or 11 wt % to 15 wt %, 20 wt %, 25 wt %, 30 wt %, 40 wt %, 45 wt %, or 50 wt %, based on the weight of the support.

In some embodiments, the support can be or can include, but is not limited to, one or more of the following compounds: $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number. BeO; MgO; CaO; BaO; SrO; $BeCG_3$; $MgCO_3$; $CaCO_3$; $SrCG_3$, $BaCG_3$; $CaZrG_3$; $Ca_7ZrAl_6O_{18}$; $CaTiG_3$; $Ca_7Al_6G_{18}$; $Ca_7HfAl_6G_{18}$; $BaCeG_3$; one or more magnesium chromates, one or more magnesium tungstates, one or more magnesium molybdates, combinations thereof, and mixtures thereof. In some embodiments, the Group 2 element can include Mg and at least a portion of the Group 2 element can be in the form of MgO or a mixed oxide that includes MgO. In some embodiments, the support can be or can include, but is not limited to, a MgO—$Al_2O_3$ mixed metal oxide. In some embodiments, when the support is a MgO—$Al_2O_3$ mixed metal oxide, the support can have a molar ratio of Mg to Al equal to 20, 10, 5, 2, 1 to 0.5, 0.1, or 0.01.

The $Mg_wAl_2O_{3+w}$, where w is a positive number, if present as the support or as a component of the support can have a molar ratio of Mg to Al in a range from 0.5, 1, 2, 3, 4, or 5 to 6, 7, 8, 9, or 10. In some embodiments, the $Mg_wAl_2O_{3+w}$ can include $MgAl_2O_4$, $Mg_2Al_2O_5$, or a mixture thereof. The $Ca_xAl_2G_{3+x}$, where x is a positive number, if present as the support or as a component of the inorganic support can have a molar ratio of Ca to Al in a range from 1:12, 1:4, 1:2, 2:3, 5:6, 1:1, 12:14, or 1.5:1. In some embodiments, the $Ca_xA12G_3$+x can include tricalcium aluminate, dodecacalcium hepta-aluminate, monocalcium aluminate, monocalcium dialuminate, monocalcium hexa-aluminate, dicalcium aluminate, pentacalcium trialuminate, tetracalcium trialuminate, or any mixture thereof. The $Sr_yAl_2G_{3+y}$, where y is a positive number, if present as the support or as a component of the support can have a molar ratio of Sr to Al in a range from 0.05, 0.3, or 0.6 to 0.9, 1.5, or 3. The $Ba_zAl_2G_{3+z}$, where z is a positive number, if present as the support or as a component of the support can have a molar ratio of Ba to Al 0.05, 0.3, or 0.6 to 0.9, 1.5, or 3.

In some embodiments, the support can also include, but is not limited to, at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga. If the support also includes a compound that includes the metal element and/or metalloid element selected from Groups other than Group 2 and Group 10, where the at least one metal element and/or at least one metalloid element is not Li, Na, K, Rb, Cs, Sn, Cu, Au, Ag, or Ga, the compound can be present in the support as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga can be or can include, but is not limited to, one or more rare earth elements, i.e., elements having an atomic number of 21, 39, or 57 to 71.

If the support includes the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga, the at least one metal element and/or at least one metalloid element can, in some embodiments, function as a binder and can be referred to as a "binder". Regardless of whether or not the at least one metal element and/or at least one metalloid element selected from Groups other than Group 2 and Group 10 and/or at least one compound thereof, where the at least one metal element and/or at least one metalloid element is not Li, Na, K, Rb, Cs, Sn, Cu, Au, Ag, or Ga, the at least one metal element and/or at least one metalloid element selected from Groups other than Group 2 and Group 10 will be further described herein as a "binder" for clarity and ease of description. In some embodiments, the support can include the binder in a range of from 0.01 wt %, 0.05 wt %, 0.1 wt %, 0.5 wt %, 1 wt %, 5 wt %, 10 wt %, 15 wt %, 20 wt %, 25 wt %, 30 wt %, 35 wt % or 40 wt % to 50 wt %, 60 wt %, 70 wt %, 80 wt %, or 90 wt % based on the weight of the support.

In some embodiments, suitable compounds that include the binder can be or can include, but are not limited to, one or more of the following: $B_2O_3$, $AlBO_3$, $Al_2O_3$, $SiO_2$, $ZrO_2$, $TiO_2$, SiC, $Si_3N_4$, an aluminosilicate, zinc aluminate, ZnO, VO, $V_2O_3$, $VO_2$, $V_2O_5$, $Ga_sO_t$, $In_uO_v$, $Mn_2O_3$, $Mn_3O_4$, MnO, one or more molybdenum oxides, one or more tungsten oxides, one or more zeolites, where s, t, u, and v are positive numbers and mixtures and combinations thereof.

The catalyst particles can have a median particle size in a range of from 1 μm, 5 μm, 10 μm, 20 μm, 40 μm, or 60 μm to 80 μm, 100 μm, 115 μm, 130 μm, 150 μm, 200 μm, 300 μm or 400, or 500 μm. The catalyst particles can have an apparent loose bulk density in a range from 0.3 g/cm$^3$, 0.4 g/cm$^3$, 0.5 g/cm$^3$, 0.6 g/cm$^3$, 0.7 g/cm$^3$, 0.8 g/cm$^3$, 0.9 g/cm$^3$, or 1 g/cm$^3$ to 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, or 2 g/cm$^3$, as measured according to ASTM D7481-18 modified with a 10, 25, or 50 mL graduated cylinder instead of a 100 or 250 mL graduated cylinder. In some embodiments, the catalyst particles can have an attrition loss after one hour of ≤5 wt %, ≤4 wt %, ≤3 wt %, ≤2 wt %, ≤1 wt %, ≤0.7 wt %, ≤0.5 wt %, ≤0.4 wt %, ≤0.3 wt %, ≤0.2 wt %, ≤0.1 wt %, ≤0.07 wt %, or ≤0.05 wt %, as measured according to ASTM D5757-11(2017). The morphology of the particles is largely spherical so that they are suitable to run in a fluid bed reactor. In some embodiments, the catalyst particles can have a size and density that is consistent with a Geldart A or Geldart B definition of a fluidizable solid.

In some embodiments, the catalyst particles can have a surface area in a range from 0.1 m$^2$/g, 1 m$^2$/g, 10 m$^2$/g, or 100 m$^2$/g to 500 m$^2$/g, 800 m$^2$/g, 1,000 m$^2$/g, or 1,500 m$^2$/g. The surface area of the catalyst particles can be measured according to the Brunauer-Emmett-Teller (BET) method using adsorption-desorption of nitrogen (temperature of liquid nitrogen, 77 K) with a Micromeritics 3flex instrument after degassing of the powders for 4 hrs at 350° C. More information regarding the method can be found, for example, in "Characterization of Porous Solids and Powders: Surface Area, Pore Size and Density," S. Lowell et al., Springer, 2004.

First Process for Making the Catalyst Composition

The process for making the catalyst composition can include preparing a slurry or gel that can include, milling, mixing, blending, combining, or otherwise contacting, but is not limited to, a compound containing a Group 2 element and a liquid medium. In some embodiments, preparation of the slurry or gel can also include contacting, but is not limited to, the compound containing a Group 2 element, the liquid medium, and one or more additives. In other embodiments, the preparing the slurry or gel can include contacting, but is not limited to, the compound containing a Group 2 element, the liquid medium, a binder or binder precursor, and, optionally, one or more additives.

The compound containing a Group 2 element can be in the form of an oxide, a hydroxide, a hydrated carbonate, a salt, a clay containing a Group 2 element, a layered double hydroxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, a silicide, or a mixture thereof. In some embodiments, the Group 2 element can be or can include Mg and the compound containing the Group 2 element can be in the form of a magnesium oxide, a magnesium hydroxide, hydromagnesite (a hydrated magnesium carbonate mineral, $Mg_5(CO_3)_4(OH)_2 \cdot 4H_2O$), a magnesium salt, a magnesium-containing clay, hydrotalcite (a layered double hydroxide), an organo-magnesium compound or a mixture thereof.

The liquid medium can be or can include, but is not limited to, water, alcohols, acetone, chloroform, methylene chloride, dimethyl formamide, dimethyl sulfoxide, glycerin, ethyl acetate, or any mixture thereof. Illustrative alcohols can be or can include, but are not limited to methanol, ethanol, isopropanol, or any mixture thereof. The binder, if present, can be or can include the binders described above. The binder precursor, if present, can be or can include, but is not limited to, $Al_2Si_2O_5(OH)_4$ (Kaolin clay), aluminum chlorohydrol, boehmite, pseudoboehmite, gibbsite, bayerite, aluminum nitrate, aluminum chloride, sodium aluminate, alumina sol, silica sol, or any mixture thereof. It is known that in literature, some of the compounds herein referred to as "binders" may also be referred to as fillers, matrix, additive, etc. The one or more additives, if present, can be or can include, but is not limited to, acids such as formic acid, lactic acid, citric acid, acetic acid, $HNO_3$, HCl, oxalic acid, stearic acid, carbonic acid, etc.; bases such as ammonia solution, NaOH, KOH, etc.; inorganic salts such as nitrates, carbonates, bicarbonates, chlorides, etc.; organic salts such as acetates, oxalates, formates, citrates, etc.; polymers such as polyvinyl alcohol, polysaccharide, etc., or any mixture thereof. The additives can help to improve the chemical/ physical property of the spray dried material and/or to improve the rheological property of the slurry/gel to facilitate spray drying.

The slurry or gel can be spray dried to produce spray dried particles that include the Group 2 element. Spray drying refers to the process of producing a dry particulate solid product from the slurry or the gel. The process can include spraying or atomizing the slurry or gel, e.g., forming small droplets, into a temperature-controlled gas stream to evaporate the liquid medium from the atomized droplets and produce the particulate solid product. For example, in the spray drying process, the slurry or gel can be atomized to small droplets and mixed with hot air or a hot inert gas, e.g., nitrogen, to evaporate the liquid from the droplets. The temperature of the slurry or gel during the spray drying process can usually be close to or greater than the boiling temperature of the liquid. An outlet air temperature of about 60° C. to about 120° C. can be common.

The slurry or gel can be atomized with one or more pressure nozzles (e.g., a fluid nozzle atomizer), one or more pulse atomizers, one or more high speed spinning discs (e.g., centrifugal or rotary atomizer), or any other known process. The median particle size, liquid (e.g., water) concentration, apparent loose bulk density, or any combination thereof, of the particulate solid product prepared via spray drying can be controlled, adjusted, or otherwise influenced by one or more operating conditions and/or parameters of the spray dryer. Illustrative operating conditions can include, but are not limited to, the feed rate and temperature of the gas stream, the atomizer velocity, the feed rate of the slurry or gel via the atomizer, the temperature of the slurry or gel, the size and/or solids concentration of the droplets, the spray dryer dimensions, or any combination thereof. It is well-known in the art that the various operating conditions will vary depending on the particular spray drying apparatus that is used and can be readily determined by persons having ordinary skill in the art.

The spray dried particles can, optionally, be calcined under an oxidative atmosphere, e.g., air, to produce calcined support particles that include the Group 2 element. In some embodiments, the spray dried particles can be calcined at a temperature in a range of from 450° C., 500° C., 525° C., 550° C., 575° C., 600° C., 625° C., 650° C., or 675° C. to 700° C., 725° C., 750° C., 775° C., 800° C., 850° C., 900° C., or 950° C. In some embodiments, the spray dried particles can be calcined at a temperature of ≤950° C., ≤900° C., ≤850° C., ≤800° C., ≤750° C., ≤700° C., ≤650° C., ≤600° C., or ≤550° C., ≤525° C., ≤500° C., ≤475° C., or ≤460° C. In some embodiments, the spray dried particles can be calcined for a time period of ≤240 minutes ≤180 minutes ≤120 minutes ≤90 minutes, ≤60 minutes, ≤45 minutes, ≤30 minutes, ≤25 minutes, ≤20 minutes, or ≤15 minutes. In some embodiments, the spray dried particles can be calcined in the presence of oxygen, e.g., air. In some embodiments, the spray dried particles can be calcined at a temperature in a range of from 550° C. to 900° C. or 550° C. to 850° C. for a time period of ≤240 minutes ≤180 minutes ≤120 minutes ≤90 minutes, ≤60 minutes, ≤45 minutes, ≤30 minutes, ≤25 minutes, ≤20 minutes, or ≤15 minutes. In other embodiments, the spray dried particles are calcined at a temperature of ≤550° C., ≤540° C., ≤530° C., ≤520° C., ≤510° C., or ≤500° C. for a time period of ≤240 minutes ≤180 minutes ≤120 minutes ≤90 minutes, ≤60 minutes, ≤45 minutes, ≤30 minutes, ≤25 minutes, ≤20 minutes, or ≤15 minutes.

The Pt present in the catalyst particles can be introduced via one or more ways. In some embodiments, the process for making the catalyst composition can include (i) contacting at least the compound containing the Group 2 element and the liquid medium with a Pt-containing compound such that the Pt can be present in the slurry or the gel and the catalyst composition can include catalyst particles that include the calcined support particles having Pt disposed thereon. In other embodiments, the process for making the catalyst composition can include (ii) depositing Pt on the spray dried particles by contacting the spray dried particles with a Pt-containing compound to produce Pt-containing spray dried particles and the catalyst composition can include catalyst particles that include the calcined support particles having Pt disposed thereon. In other embodiments, the process for making the catalyst composition can include (iii) depositing Pt on the calcined support particles if the spray dried particles are optionally calcined by contacting the calcined support particles with a Pt-containing compound to produce Pt-containing calcined support particles and the process can, optionally, further include calcining the Pt-containing calcined support particles to produce re-calcined support particles having Pt disposed thereon, where the catalyst composition can include the re-calcined support particles. In some embodiments, the catalyst composition can include the Pt-containing calcined support particles without the optional additional calcination step. In other embodiments, the process for making the catalyst composition can include option (i), (ii), (iii), (i) and (ii), (i) and (iii), (ii) and (iii), or (i), (ii), and (iii). The Pt-containing compound can be or can include, but is not limited to, chloroplatinic acid hexahydrate, tetraammineplatinum(II) nitrate, platinum(II) acetylacetonate, platinum(II) bromide, platinum(II) iodide, platinum(II) chloride, platinum(IV) chloride, platinum(II)diammine dichloride, ammonium tetrachloroplatinate(II), tetraammineplatinum(II) chloride hydrate, tetraammineplatinum(II) hydroxide hydrate, or any mixture thereof.

The promoter present in the catalyst particles can be introduced via one or more ways. In some embodiments, the process for making the catalyst composition can include (iv) contacting at least the compound containing the Group 2 element and the liquid medium with a compound that includes a promoter element such that the promoter element is present in the slurry or the gel and the catalyst composition can include catalyst particles that include the calcined support particles having the promoter element disposed thereon. In other embodiments, the process for making the catalyst composition can include (v) depositing a compound that includes a promoter element on the spray dried particles to produce promoter-containing spray dried particles and the catalyst composition can include catalyst particles that include the calcined support particles having the promoter element disposed thereon. In other embodiments, the process for making the catalyst composition can include (vi) depositing a compound that includes a promoter element on the calcined support particles if the spray dried particles are optionally calcined to produce promoter-containing calcined support particles and the process can further include, optionally, calcining the promoter-containing calcined support particles to produce re-calcined support particles having the promoter element disposed thereon, where the catalyst composition includes the re-calcined support particles. In some embodiments, the catalyst composition can include the promoter-containing calcined support particles without the optional additional calcination step. In other embodiments, the process for making the catalyst composition can include option (iv), (v), (vi), (iv) and (v), (iv) and (vi), (v) and (vi), or (iv), (v), and (vi). In other embodiments, the process can include any one or more of options (i), (ii), and (iii) and any one or more of options (iv), (v), and (iv). The compound that includes the promoter element can be or can include, but is not limited to, tin(II) oxide, tin(IV) oxide, tin(IV) chloride pentahydrate, tin(II) chloride dihydrate, tin(II) bromide, tin(IV) bromide, tin(II) acetylacetonate, tin(II) acetate, tin (IV) acetate, silver(I) nitrate, gold(III) nitrate, copper(II) nitrate, gallium(III) nitrate, or any mixture thereof.

The alkali metal element, if present in the catalyst particles, can be introduced via one or more ways. In some embodiments, the process for making the catalyst composition can include (vii) contacting at least the compound containing the Group 2 element and the liquid medium with a compound that includes an alkali metal element such that the alkali metal element is present in the slurry or the gel and the catalyst composition can include catalyst particles that include the calcined support particles having the alkali metal element disposed thereon. In other embodiments, the process for making the catalyst composition can include (viii) depositing a compound that includes an alkali metal element on the spray dried particles to produce alkali metal element-containing spray dried particles and the catalyst composition can include catalyst particles that include the calcined support particles having the alkali metal element disposed thereon. In other embodiments, the process for making the catalyst composition can include (ix) depositing a compound that includes an alkali metal element on the calcined support particles if the spray dried particles are optionally calcined to produce alkali metal element-containing calcined support particles and the process can further include, optionally, calcining the alkali metal element-containing calcined support particles to produce re-calcined support particles having the alkali metal element disposed thereon, where the catalyst composition includes the re-calcined support particles. In other embodiments, the process for making the catalyst composition can include option (vii), (viii), (ix), (vii) and (viii), (vi) and (ix), (viii) and (ix), or (vii), (viii), and (iv). In other embodiments, the process can include any one or more of options (i), (ii), and (iii), any one or more of options (iv), (v), and (iv), and any one or more of options (vii), (viii), and (ix). The compound that includes the alkali metal element can be or can include, but are not limited to, lithium nitrate, sodium nitrate, potassium nitrate, rubidium nitrate, cesium nitrate, or any mixture thereof.

In some embodiments, the process for making the catalyst composition can optionally include hydrating the calcined support particles to produce hydrated support particles. For example, the calcined support particles can be contacted with water to produce the hydrated support particles. In such embodiment, the process can also include calcining the hydrated support particles to produce the catalyst composition that includes re-calcined support particles. Hydrating the calcined support can be carried out at a temperature in a range of from 20° C., 40° C., or 60° C. to 80° C., 120° C., 140° C., 160° C., 180° C., or 200° C. The calcined support can be contacted with the water for a time period in a range of from 1 minutes, 5 minutes, or 10 minutes to 20 minutes, 40 minutes, 80 minutes, 160 minutes, 6 hours, 12 hours, 24 hours, or 48 hours. In some embodiments, an anion such as chloride, nitrate, carbonate, bicarbonate, acetate, oxalate, formate, and/or citrate can be present during hydration.

In some embodiments, the process for making the catalyst composition can optionally include hydrating the spray dried particles to produce hydrated spray dried particles. For example, the spray dried particles can be contacted with water to produce the hydrated spray dried particles. In such embodiment, the process can also include calcining the hydrated spray dried particles to produce the catalyst composition that includes calcined support particles. Hydrating the spray dried particles can be carried out at a temperature in a range of from 20° C., 40° C., or 60° C. to 80° C., 120° C., 140° C., 160° C., 180° C., or 200° C. The spray dried particles can be contacted with the water for a time period in a range of from 1 minutes, 5 minutes, or 10 minutes to 20 minutes, 40 minutes, 80 minutes, 160 minutes, 6 hours, 12 hours, 24 hours, or 48 hours. In some embodiments, an anion such as chloride, nitrate, carbonate, bicarbonate, acetate, oxalate, formate, and/or citrate can be present during hydration.

In some embodiments, the process for making the catalyst composition can optionally include hydrating the spray dried particles to produce hydrated spray dried particles, calcining the hydrated spray dried particles to produce calcined support particles, hydrating the calcined support particles to produce hydrated calcined support particles, and calcining the hydrated calcined support particles to produce re-calcined support particles. As such, the catalyst composition can include the spray dried particles, the calcined support particles, the hydrated spray dried particles, the hydrated spray dried particles that can be calcined, the hydrated calcined support particles, the hydrated calcined support particles that can be re-calcined, or any mixture thereof.

In some embodiments, catalysts particles produced by hydrating the calcined support particles or the spray dried particles and then calcining the hydrated calcined support particles or the hydrated spray dried particles can produce catalyst particles that have an attrition loss after one hour that is less than an attrition loss after one hour of the initially calcined particles or the spray dried particles produced before the hydration step, as measured according to ASTM D5757-11(2017). In some embodiments, catalysts particles produced by hydrating the calcined support particles or the spray dried particles and then calcining the hydrated support particles or the hydrated support particles can produce catalyst particles that have an attrition loss after one hour that is 10% less, 30% less, 50% less, 70% less, 90% less, or 100% less, than an attrition loss after one hour of the initially calcined particles produced before the hydration step, as measured according to ASTM D5757-11(2017).

Second Process for Making the Catalyst Composition

In some embodiments, the catalyst particles can be catalyst particles produced through only the spray drying step such that the slurry is prepared and spray dried particles are produced therefrom with the Pt and promoter added to the slurry, the spray dried particles, or a combination thereof. Accordingly, in some embodiments the process for making a catalyst composition, can include preparing the slurry or gel that can include the compound containing a Group 2 element and a liquid medium and optionally one or more additives as described above and spray drying the slurry or the gel to produce spray dried support particles that include the Group 2 element. At least one of (i) and (ii) can be met: (i) Pt can be present in the slurry or the gel in the form of the Pt-containing compound and the catalyst composition can include catalyst particles that include the spray dried support particles having Pt disposed thereon, and (ii) Pt can be deposited on the spray dried support particles by contacting the spray dried support particles with the Pt-containing compound to produce Pt-containing spray dried support particles and the catalyst composition can include catalyst particles that can include the spray dried support particles having Pt disposed thereon. At least one of (iii) and (iv) can also be met: (iii) the compound that includes the promoter element can present in the slurry or the gel and the catalyst composition can include catalyst particles that include the spray dried support particles having the promoter element disposed thereon, and (iv) the compound that can include the promoter element can be deposited on the spray dried support particles to produce promoter-containing spray dried support particles and the catalyst composition can include catalyst particles that include the spray dried support particles having the promoter element disposed thereon, where the promoter element includes Sn, Cu, Au, Ag, Ga, or a combination thereof, or a mixture thereof. In some embodiments, the optional alkali metal element(s) and/or binders can also be added during the synthesis of the catalyst particles as described above.

In such embodiments, the catalyst particles can be further processed or activated in-situ by adding the catalyst particles into a hydrocarbon upgrading process that subjects the catalyst particles to higher severity conditions to produce catalyst particles having a greater level of activation than just the spray dried particles have upon preparation thereof. In some embodiments, when the catalyst particles include catalyst particles only subjected to the spray drying step such that the slurry is prepared and spray dried support particles are produced therefrom with the Pt and promoter added to the slurry, the spray dried support particles, or a combination thereof, the catalyst particles can be introduced into a reaction zone, a combustion zone, a reduction zone, or any other location within a fluidized hydrocarbon upgrading process some of which are further described below.

The preparation of the catalyst composition and processes for adding Pt, the promoter(s) such as Sn, the optional alkali metal element(s), and the optional rare earth metal element(s) to the catalyst composition has been described above. In some embodiments, the preparation of the slurry or gel, spray drying the slurry, calcination of the spray dried particles and/or the hydrated calcined particles, and/or hydration of the Group 2 metal containing calcined support particles or the spray-dried particles can also be performed using one of the known methods reported in literature, such as U.S. Pat. Nos. 4,866,019; 6,028,023; 6,589,902; 6,593,265; 6,800,578; 7,361,264; and 7,417,005; U.S. Patent Application Publication Nos. 2004/0029729; 2005/000396; and 2016/0082424; WO Publication No. WO2008083563A1; and journal publications Wang et al., *Ind. Eng. Chem. Res.* 2008, 47, 5746-5750; Chubar et al., *Chem. Eng. J.* 2013, 234, 284-299; Valente et al., *Energy Environ. Sci.,* 2011, 4, 4096-4107; and Julklang et al., *Mater. Lett.* 2017, 209, 429-432.

A First Process for Upgrading a Hydrocarbon

The first process for upgrading a hydrocarbon can include contacting a first hydrocarbon-containing feed with the catalyst composition that includes the catalyst particles that include Pt and the promoter disposed on the support to effect one or more of dehydrogenation, dehydroaromatization, and dehydrocyclization of at least a portion of the first hydrocarbon-containing feed to produce a coked catalyst and an effluent that can include one or more upgraded hydrocarbons and molecular hydrogen. The catalyst composition and the first hydrocarbon-containing feed can be contacted with one another within any suitable environment such as one or more reaction or conversion zones disposed within one or more reactors to produce the effluent and the coked catalyst. The reaction or conversion zone can be disposed or otherwise located within one or more fixed bed reactors, one or more fluidized or moving bed reactors, one or more reverse flow reactors, or any combination thereof.

The first hydrocarbon-containing feed and catalyst composition can be contacted at a temperature in a range from 300° C., 350° C., 400° C., 450° C., 500° C., 550° C., 600° C., 620° C., 650° C., 660° C., 670° C., 680° C., 690° C., or 700° C. to 725° C., 750° C., 760° C., 780° C., 800° C., 825° C., 850° C., 875° C., or 900° C. In some embodiments, the first hydrocarbon-containing feed and the catalyst composition can be contacted at a temperature of at least 620° C., at least 650° C., at least 660° C., at least 670° C., at least 680° C., at least 690° C., or at least 700° C. to 725° C., 750° C., 760° C., 780° C., 800° C., 825° C., 850° C., 875° C., or 900° C. The first hydrocarbon-containing feed can be introduced into the reaction or conversion zone and contacted with the catalyst composition therein for a time period of ≤3 hours, ≤2.5 hours, ≤2 hours, ≤1.5 hours, ≤1 hour, ≤45 minutes, ≤30 minutes, ≤20 minutes, ≤10 minutes, ≤5 minutes, ≤1 minute, ≤30 seconds, ≤10 seconds, ≤5 seconds, or ≤1 second or ≤0.5 second. In some embodiments, the first hydrocarbon-containing feed can be contacted with the catalyst composition for a time period in a range from 0.1 seconds, 0.5 seconds, 0.7 seconds, 1 second, 30 second, 1 minute, 5 minutes, or 10 minutes to 30 minutes, 50 minutes, 70 minutes, 1.5 hours, 2 hours, or 3 hours.

The first hydrocarbon-containing feed and the catalyst composition can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the first hydrocarbon-containing feed. In some embodiments, the hydrocarbon partial pressure during contact of the first hydrocarbon-containing feed and the catalyst composition can be in a range from 20 kPa-absolute, 50 kPa-absolute, 100 kPa-absolute, at least 150 kPa, at least 200 kPa 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute, where the hydrocarbon partial pressure is the total partial pressure of any $C_2$-$C_{16}$ alkanes and any $C_8$-$C_{16}$ alkyl aromatics in the first hydrocarbon-containing feed. In other embodiments, the hydrocarbon partial pressure during contact of the hydrocarbon-containing feed and the catalyst composition can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute, where the hydrocarbon partial pressure is the total partial pressure of any $C_2$-$C_{16}$ alkanes and any $C_8$-$C_{16}$ alkyl aromatics in the first hydrocarbon-containing feed.

In some embodiments, the first hydrocarbon-containing feed can include at least 60 vol %, at least 65 vol %, at least 70 vol %, at least 75 vol %, at least 80 vol %, at least 85 vol %, at least 90 vol %, at least 95 vol %, or at least 99 vol % of a single $C_2$-$C_{16}$ alkane, e.g., propane, based on a total volume of the first hydrocarbon-containing feed. The first hydrocarbon-containing feed and catalyst composition can be contacted under a single $C_2$-$C_{16}$ alkane, e.g., propane, pressure of at least 20 kPa-absolute, at least 50 kPa-absolute, at least 100 kPa-absolute, at least 150 kPa-absolute, at least 250 kPa-absolute, at least 300 kPa-absolute, at least 400 kPa-absolute, at least 500 kPa-absolute, or at least 1,000 kPa-absolute.

The first hydrocarbon-containing feed can be contacted with the catalyst composition within the reaction or conversion zone at any weight hourly space velocity (WHSV) effective for carrying out the upgrading process. In some embodiments, the WHSV can be 0.01 $hr^{-1}$, 0.1 $hr^{-1}$, 1 $hr^{-1}$, 2 $hr^{-1}$, 5 $hr^{-1}$, 10 $hr^{-1}$, 20 $hr^{-1}$, 30 $hr^{-1}$, or 50 $hr^{-1}$ to 100 $hr^{-1}$, 250 $hr^{-1}$, 500 $hr^{-1}$, or 1,000 $hr^{-1}$. In some embodiments, when the hydrocarbon upgrading process includes a fluidized or otherwise moving catalyst composition, a ratio of the catalyst composition circulation mass flow rate to a combined amount of any $C_2$-$C_{16}$ alkanes and any $C_8$-$C_{16}$ alkyl aromatics mass flow rate can be in a range from 1, 3, 5, 10, 15, 20, 25, 30, or 40 to 50, 60, 70, 80, 90, 100, 110, 125, or 150 on a weight to weight basis.

When the activity of the coked catalyst decreases below a desired minimum amount, the coked catalyst or at least a portion thereof can be subjected to a regeneration process to produce a regenerated catalyst. More particularly, the coked catalyst can be contacted with one or more oxidants to effect combustion of at least a portion of the coke to produce a regenerated catalyst lean in coke and a combustion gas. Regeneration of the coked catalyst can occur within the reaction or conversion zone or within a combustion zone that is separate and apart from the reaction or conversion zone, depending on the particular reactor configuration, to produce a regenerated catalyst. For example, regeneration of the coked catalyst can occur within the reaction or conversion zone when a fixed bed or reverse flow reactor is used, or within a separate combustion zone that can be separate and apart from the reaction or conversion zone when a fluidized bed reactor or other circulating or fluidized type reactor is used.

In some embodiments the process can optionally include contacting at least a portion of the regenerated catalyst with a reducing gas to produce a regenerated and reduced catalyst. An additional quantity of the hydrocarbon-containing feed can be contacted with at least a portion of the regenerated catalyst and/or at least a portion of any regenerated and reduced catalyst to produce a re-coked catalyst and additional effluent.

In some embodiments, a cycle time from contacting the hydrocarbon-containing feed with the catalyst to contacting the additional quantity of the hydrocarbon-containing feed with the regenerated catalyst can be ≤5 hours. The first cycle begins upon contact of the catalyst composition with the first hydrocarbon-containing feed, followed by contact with at least the oxidative gas to produce the regenerated catalyst or at least the oxidative gas and the optional reducing gas to produce the regenerated catalyst, and the first cycle ends upon contact of the regenerated catalyst with the additional quantity of the first hydrocarbon-containing feed. If one or more additional feeds (described in more detail below) are utilized between flows of the first hydrocarbon-containing feed and the oxidative gas, between the oxidative gas and the reducing gas (if used), between the oxidative gas and the additional quantity of the first hydrocarbon-containing feed, and/or between the reducing gas (if used) and the additional quantity of the first hydrocarbon-containing feed, the period of time such stripping gas(es) is/are utilized would be included in the period included in the cycle time. As such, the cycle time from contacting the first hydrocarbon-containing feed with the catalyst in step to the contacting the additional quantity of the hydrocarbon-containing feed with the regenerated catalyst, in some embodiments, can be ≤5 hours.

The oxidant can be or can include, but is not limited to, $O_2$, $O_3$, $CO_2$, $H_2O$, or a mixture thereof. In some embodiments, an amount of oxidant in excess of that needed to combust 100% of the coke on the catalyst can be used to increase the rate of coke removal from the catalyst, so that the time needed for coke removal can be reduced and lead to an increased yield in the upgraded product produced within a given period of time. The use of pure $O_2$ as an oxidant can facilitate the capturing and sequestration of $CO_2$ made during combustion in one or more downstream $CO_2$ recovery systems.

The coked catalyst and oxidant can be contacted with one another at a temperature in a range from 500° C., 550° C., 600° C., 650° C., 700° C., 750° C., or 800° C. to 900° C., 950° C., 1,000° C., 1,050° C., or 1,100° C. to produce the regenerated catalyst. In some embodiments, the coked catalyst and oxidant can be contacted with one another at a temperature in a range from 500° C. to 1,100° C., 600° C. to 1,000° C., 650° C. to 950° C., 700° C. to 900° C., or 750° C. to 850° C. to produce the regenerated catalyst.

The coked catalyst and oxidant can be contacted with one another for a time period of ≤2 hours, ≤1 hour, ≤30 minutes, ≤10 minutes, ≤5 minutes, ≤1 min, ≤30 seconds, ≤10 seconds, ≤5 seconds, or ≤1 second. For example, the coked catalyst and oxidant can be contacted with one another for a time period in a range from 2 seconds to 2 hours. In some embodiments, the coked catalyst and oxidant can be contacted for a time period sufficient to remove ≥50 wt %, ≥75 wt %, or ≥90 wt % or ≥99% of any coke disposed on the catalyst.

In some embodiments, the time period the coked catalyst and oxidant contact one another can be less than the time period the catalyst contacts the hydrocarbon-containing feed to produce the effluent and the coked catalyst. For example, the time period the coked catalyst and oxidant contact one another can be at least 90%, at least 60%, at least 30%, or at least 10% less than the time period the catalyst contacts the hydrocarbon-containing feed to produce the effluent. In other embodiments, the time period the coked catalyst and oxidant contact one another can be greater than the time period the catalyst contacts the hydrocarbon-containing feed to produce the effluent and the coked catalyst. For example, the coked catalyst and oxidant contact one another can be at least 50%, at least 100%, at least 300%, at least 500%, at least 1,000%, at least 10,000%, at least 30,000%, at least 50,000%, at least 75,000%, at least 100,000%, at least 250,000%, at least 500,000%, at least 750,000%, at least 1,000,000%, at least 1,250,000%, at least 1,500,000%, or at least 1,800,000% greater than the time period the catalyst contacts the hydrocarbon-containing feed to produce the effluent.

The coked catalyst and oxidant can be contacted with one another under an oxidant partial pressure in a range from 20 kPa-absolute, 50 kPa-absolute, 100 kPa-absolute, 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute. In other embodiments, the oxidant partial pressure during contact with the coked catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute to produce the regenerated catalyst.

Without wishing to be bound by theory, it is believed that at least a portion of the Pt and, if present, and Ni and/or Pd, disposed on the coked catalyst can be agglomerated as compared to the catalyst prior to contact with the first hydrocarbon-containing feed. It is believed that during combustion of at least a portion of the coke on the coked catalyst that at least a portion of the Pt and, if present, any Ni and/or Pd can be re-dispersed about the support. Re-dispersing at least a portion of any agglomerated Pt and, if present, Ni and/or Pd can increase the activity and improve the stability of the catalyst over many cycles.

In some embodiments, at least a portion of the Pt and, if present, Ni and/or Pd in the regenerated catalyst can be at a higher oxidized state as compared to the Pt and, if present, Ni and/or Pd in the catalyst contacted with the first hydrocarbon-containing feed and as compared to the Pt and, if present, Ni and/or Pd in the coked catalyst. As such, as noted above, in some embodiments the process can optionally include contacting at least a portion of the regenerated catalyst with a reducing gas to produce a regenerated and reduced catalyst. Suitable reducing gases (reducing agent) can be or can include, but are not limited to, $H_2$, CO, $CH_4$, $C_2H_6$, $C_3H_8$, $C_2H_4$, $C_3H_6$, steam, or a mixture thereof. In some embodiments, the reducing agent can be mixed with an inert gas such as Ar, Ne, He, $N_2$, $CO_2$, $H_2O$ or a mixture thereof. In such embodiments, at least a portion of the Pt and, if present Ni and/or Pd, in the regenerated and reduced catalyst can be reduced to a lower oxidation state, e.g., the elemental state, as compared to the Pt and, if present, Ni and/or Pd in the regenerated catalyst. In this embodiment, the additional quantity of the hydrocarbon-containing feed can be contacted with at least a portion of the regenerated catalyst and/or at least a portion of the regenerated and reduced catalyst.

In some embodiments, the regenerated catalyst and the reducing gas can be contacted at a temperature in a range from 400° C., 450° C., 500° C., 550° C., 600° C., 620° C., 650° C., or 670° C. to 720° C., 750° C., 800° C., or 900° C. The regenerated catalyst and the reducing gas can be contacted for a time period in a range from 1 second, 5 seconds, 10 seconds, 20 seconds, 30 seconds, or 1 minute to 10 minutes, 30 minutes, or 60 minutes. The regenerated catalyst and reducing gas can be contacted at a reducing agent partial pressure of 20 kPa-absolute, 50 kPa-absolute, or 100 kPa-absolute, 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute. In other embodiments, the reducing agent partial pressure during contact with the regenerated catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute to produce the regenerated catalyst.

At least a portion of the regenerated catalyst, the regenerated and reduced catalyst, new or fresh catalyst, or a mixture thereof can be contacted with an additional quantity of the first hydrocarbon-containing feed within the reaction or conversion zone to produce additional effluent and additional coked catalyst. As noted above, in some embodiments, the cycle time from the contacting the hydrocarbon-containing feed with the catalyst to the contacting the additional quantity of the hydrocarbon-containing feed with at least a portion of the regenerated catalyst, and/or the regenerated and reduced catalyst, and optionally with new or fresh catalyst can be ≤5 hours.

In some embodiments, as noted above, one or more additional feeds, e.g., one or more sweep fluids, can be utilized between flows of the first hydrocarbon-containing feed and the oxidant, between the oxidant and the optional reducing gas if used, between the oxidant and the additional first hydrocarbon-containing feed, and/or between the reducing gas and the additional first hydrocarbon-containing feed. The sweep fluid can, among other things, purge or otherwise urge undesired material from the reactors, such as non-combustible particulates including soot. In some embodiments, the additional feed(s) can be inert under the dehydrogenation, dehydroaromatization, and dehydrocyclization, combustion, and/or reducing conditions. Suitable sweep fluids can be or can include, but are not limited to, $N_2$, He, Ar, $CO_2$, $H_2O$, $CO_2$, $CH_4$, or a mixture thereof. In some embodiments, if the process utilizes a sweep fluid the duration or time period the sweep fluid is used can be in a range from 1 second, 5 seconds, 10 seconds, 20 seconds, 30 seconds, or 1 minute to 10 minutes, 30 minutes, or 60 minutes.

In some embodiments, the catalyst composition can remain sufficiently active and stable after many cycles, e.g., at least 15, at least 20, at least 30, at least 40, at least 50, at least 60, at least 70, at least 100 cycles, at least 125 cycles, at least 150 cycles, at least 175 cycles, or at least 200 cycles with each cycle time lasting for ≤5 hours, ≤4 hours, ≤3 hours, ≤2 hours, ≤1 hour, ≤50 minutes, ≤45 minutes, ≤30 minutes, ≤15 minutes, ≤10 minutes, ≤5 minutes, ≤1 minute, ≤30 seconds, or ≤10 seconds. In some embodiments, the cycle time can be from 5 seconds, 30 seconds, 1 minute or 5 minutes to 10 minutes, 20 minutes, 30 minutes, 45 minutes, 50 minutes, 70 minutes, 2 hours, 3 ours, 4 hours, or 5 hours. In some embodiments, after the catalyst composition performance stabilizes (sometimes the first few cycles can have a relatively poor or a relatively good performance, but the performance can eventually stabilize), the process can produce a first upgraded hydrocarbon product yield, e.g., propylene when the hydrocarbon-containing feed includes propane, at an upgraded hydrocarbon selectivity, e.g., propylene, of ≥75%, ≥80%, ≥85%, or ≥90%, or ≥95% when initially contacted with the first hydrocarbon-containing feed, and can have a second upgraded hydrocarbon product yield upon completion of the last cycle (at least 15 cycles total) that can be at least 90%, at least 93%, at least 95%, at least 97%, at least 98%, at least 99%, at least 99.5%, or at least 100% of the first upgraded hydrocarbon product yield at an upgraded hydrocarbon selectivity, e.g., propylene, of ≥75%, ≥80%, ≥85%, or ≥90%, or ≥95%.

In some embodiments, when the first hydrocarbon-containing feed includes propane and the upgraded hydrocarbon includes propylene, contacting the hydrocarbon-containing feed with the catalyst composition can produce a propylene yield of ≥48%, ≥49%, ≥50%, ≥51%, ≥52%, ≥53%, ≥54%, ≥55%, ≥56%, ≥57%, ≥58%, ≥59%, ≥60%, ≥61%, ≥62%, ≥63%, ≥64%, ≥65%, or ≥66% at a propylene selectivity of ≥75%, ≥80%, ≥85%, ≥90%, ≥93%, or ≥95%. In some embodiments, when the hydrocarbon-containing feed includes propane and the upgraded hydrocarbon includes propylene, contacting the hydrocarbon-containing feed with the catalyst composition can produce a propylene yield of at least 48%, at least 49%, at least 50%, at least 51%, at least 52%, at least 53%, at least 55%, at least 57%, at least 60%, at least 62%, at least 63%, at least 64%, at least 65%, at or at least 66% at a propylene selectivity of at least 75%, at least 80%, at least 85%, at least 90%, or at least 95% for at least 15, at least 20, at least 30, at least 40, at least 50, at least 60, at least 70, at least 100 cycles, at least 125 cycles, at least 150 cycles, at least 175 cycles, or at least 200 cycles. In other embodiments, when the hydrocarbon-containing feed includes at least 70 vol %, at least 75 vol %, at least 80 vol %, at least 85 vol %, at least 90 vol %, or at least 95 vol % of propane, based on a total volume of the first hydrocarbon-containing feed, is contacted under a propane partial pressure of at least 20 kPa-absolute, a propylene yield of at least 48%, at least 49%, at least 50%, at least 51%, at least 52%, at least 53%, at least 55%, at least 57%, at least 60%, at least 62%, at least 63%, at least 64%, at least 65%, or at least 66% at a propylene selectivity of at least 75%, at least 80%, at least 85%, at least 90%, or at least 95% can be obtained for at least 15, at least 20, at least 30, at least 40, at least 50, at least 60, at least 70, at least 100 cycles, at least 125 cycles, at least 150 cycles, at least 175 cycles, or at least 200 cycles. It is believed that the propylene yield can be further increased to at least 67%, at least 68%, at least 70%, at least 72%, at least 75%, at least 77%, at least 80%, or at least 82% at a propylene selectivity of at least 75%, at least 80%, at least 85%, at least 90%, or at least 95% for at least 15 cycles, at least 20, at least 30, at least 40, at least 50, at least 60, at least 70, at least 100 cycles, at least 125 cycles, at least 150 cycles, at least 175 cycles, or at least 200 cycles by further optimizing the composition of the support and/or adjusting one or more process conditions. In some embodiments, the propylene yield can be obtained when the catalyst composition is contacted with the hydrocarbon-containing feed at a temperature of at least 620° C., at least 630° C., at least 640° C., at least 650° C., at least 655° C., at least 660° C., at least 670° C., at least 680° C., at least 690° C., at least 700° C., or at least 750° C. for at least 15, at least 20, at least 30, at least 40, at least 50, at least 60, at least 70, at least 100 cycles, at least 125 cycles, at least 150 cycles, at least 175 cycles, or at least 200 cycles.

Systems suitable for carrying out the processes disclosed herein can include systems that are well-known in the art such as the fixed bed reactors disclosed in WO Publication No. WO2017078894; the fluidized riser reactors and/or downer reactors disclosed in U.S. Pat. Nos. 3,888,762; 7,102,050; 7,195,741; 7,122,160; and 8,653,317; and U.S. Patent Application Publication Nos. 2004/0082824; 2008/0194891; and the reverse flow reactors disclosed in U.S. Pat. No. 8,754,276; U.S. Patent Application Publication No. 2015/0065767; and WO Publication No. WO2013169461.

The first hydrocarbon-containing feed can be or can include, but is not limited to, one or more alkane hydrocarbons, e.g., $C_2$-$C_{16}$ linear or branched alkanes and/or $C_4$-$C_{16}$ cyclic alkanes, and/or one or more alkyl aromatic hydrocarbons, e.g., $C_8$-$C_{16}$ alkyl aromatics. In some embodiments, the first hydrocarbon-containing feed can optionally include 0.1 vol % to 50 vol % of steam, based on a total volume of any $C_2$-$C_{16}$ alkanes and any $C_8$-$C_{16}$ alkyl aromatics in the hydrocarbon-containing feed. In other embodiments, the first hydrocarbon-containing feed can include <0.1 vol % of steam or can be free of steam, based on the total volume of any $C_2$-$C_{16}$ alkanes and any $C_8$-$C_{16}$ alkyl aromatics in the hydrocarbon-containing feed.

The $C_2$-$C_{16}$ alkanes can be or can include, but are not limited to, ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, or a mixture thereof. For example, the first hydrocarbon-containing feed can include propane, which can be dehydrogenated to produce propylene, and/or isobutane, which can be dehydrogenated to produce isobutylene. In another example, the first hydrocarbon-containing feed can include liquid petroleum gas (LP gas), which can be in the gaseous phase when contacted with the catalyst. In some embodiments, the first hydrocarbon in the hydrocarbon-containing feed can be composed of substantially a single alkane such as propane. In some embodiments, the hydrocarbon-containing feed can include ≥50 mol %, ≥75 mol %, ≥95 mol %, ≥98 mol %, or ≥99 mol % of a single $C_2$-$C_{16}$ alkane, e.g., propane, based on a total weight of all hydrocarbons in the first hydrocarbon-containing feed. In some embodiments, the first hydrocarbon-containing feed can include at least 50 vol %, at least 55 vol %, at least 60 vol %, at least 65 vol %, at least 70 vol %, at least 75 vol %, at least 80 vol %, at least 85 vol %, at least 90 vol %, at least 95 vol %, at least 97 vol %, or at least 99 vol % of a single $C_2$-$C_{16}$ alkane, e.g., propane, based on a total volume of the first hydrocarbon-containing feed.

The $C_8$-$C_{16}$ alkyl aromatics can be or can include, but are not limited to, ethylbenzene, propylbenzene, butylbenzene, one or more ethyl toluenes, or a mixture thereof. In some embodiments, the hydrocarbon-containing feed can include ≥50 mol %, ≥75 mol %, ≥95 mol %, ≥98 mol %, or ≥99 mol % of a single $C_8$-$C_{16}$ alkyl aromatic, e.g., ethylbenzene, based on a total weight of all hydrocarbons in the first hydrocarbon-containing feed. In some embodiments, the ethylbenzene can be dehydrogenated to produce styrene. As such, in some embodiments, the first process for upgrading a hydrocarbon disclosed herein can include propane dehydrogenation, butane dehydrogenation, isobutane dehydrogenation, pentane dehydrogenation, pentane dehydrocyclization to cyclopentadiene, naphtha reforming, ethylbenzene dehydrogenation, ethyltoluene dehydrogenation, and the like.

In some embodiments, the first hydrocarbon-containing feed can be diluted, e.g., with one or more diluents such as one or more inert gases. Suitable inert gases can be or can include, but are not limited to, Ar, Ne, He, $N_2$, $CO_2$, $CH_4$, or a mixture thereof. If the hydrocarbon containing-feed includes a diluent, the hydrocarbon-containing feed can include 0.1 vol %, 0.5 vol %, 1 vol %, or 2 vol % to 3 vol %, 8 vol %, 16 vol %, or 32 vol % of the diluent, based on a total volume of any $C_2$-$C_{16}$ alkanes and any $C_8$-$C_{16}$ alkyl aromatics in the hydrocarbon-containing feed.

In some embodiments, the first hydrocarbon-containing feed can also include $H_2$. In some embodiments, when the first hydrocarbon-containing feed includes $H_2$, a molar ratio of the $H_2$ to a combined amount of any $C_2$-$C_{16}$ alkane and any $C_8$-$C_{16}$ alkyl aromatic can be in a range from 0.1, 0.3, 0.5, 0.7, or 1 to 2, 3, 4, 5, 6, 7, 8, 9, or 10.

In some embodiments, the first hydrocarbon-containing feed can be substantially free of any steam, e.g., <0.1 vol % of steam, based on a total volume of any $C_2$-$C_{16}$ alkanes and any C8-$C_{16}$ alkyl aromatics in the hydrocarbon-containing feed. In other embodiments, the first hydrocarbon-containing feed can include steam. For example, the first hydrocarbon-containing feed can include 0.1 vol %, 0.3 vol %, 0.5 vol %, 0.7 vol %, 1 vol %, 3 vol %, or 5 vol % to 10 vol %, 15 vol %, 20 vol %, 25 vol %, 30 vol %, 35 vol %, 40 vol %, 45 vol %, or 50 vol % of steam, based on a total volume of any $C_2$-$C_{16}$ alkanes and any $C_8$-$C_{16}$ alkyl aromatics in the first hydrocarbon-containing feed. In other embodiments, the first hydrocarbon-containing feed can include ≤50 vol %, ≤45 vol %, ≤40 vol %, ≤35 vol %, ≤30 vol %, ≤25 vol %, ≤20 vol %, or ≤15 vol % of steam, based on a total volume of any $C_2$-$C_{16}$ alkanes and any $C_8$-$C_{16}$ alkyl aromatics in the first hydrocarbon-containing feed. In other embodiments, the first hydrocarbon-containing feed can include at least 1 vol %, at least 3 vol %, at least 5 vol %, at least 10 vol %, at least 15 vol %, at least 20 vol %, at least 25 vol %, or at least 30 vol % of steam, based on a total volume of any $C_2$-$C_{16}$ alkanes and any $C_8$-$C_{16}$ alkyl aromatics in the first hydrocarbon-containing feed.

In some embodiments, the first hydrocarbon-containing feed can include sulfur. For example, the first hydrocarbon-containing feed can include sulfur in a range from 0.5 ppm, 1 ppm, 5 ppm, 10 ppm, 20 ppm 30 ppm, 40 ppm, 50 ppm, 60 ppm, 70 ppm, or 80 ppm to 100 ppm, 150 ppm, 200 ppm, 300 ppm, 400 ppm, or 500 ppm. In other embodiments, the first hydrocarbon-containing feed can include sulfur in a range from 1 ppm to 10 ppm, 10 ppm to 20 ppm, 20 ppm to 50 ppm, 50 ppm to 100 ppm, or 100 ppm to 500 ppm. The sulfur, if present in the first hydrocarbon-containing feed, can be or can include, but is not limited to, H2S, dimethyl disulfide, as one or more mercaptans, or any mixture thereof.

In some embodiments, the first hydrocarbon-containing feed can be substantially free or free of molecular oxygen. In some embodiments, the first hydrocarbon-containing feed can include ≤5 mol %, ≤3 mol %, or ≤1 mol % of molecular oxygen (O2). It is believed that providing a first hydrocarbon-containing feed substantially-free of molecular oxygen substantially prevents oxidative reactions that would otherwise consume at least a portion of the alkane and/or the alkyl aromatic in the first hydrocarbon-containing feed.

Recovery and Use of the First Upgraded Hydrocarbon

In some embodiments, the first upgraded hydrocarbon can include at least one upgraded hydrocarbon, e.g., an olefin, water, unreacted hydrocarbons, molecular hydrogen, etc. The first upgraded hydrocarbon can be recovered or otherwise obtained via any convenient process, e.g., by one or more conventional processes. One such process can include cooling and/or compressing the effluent to condense at least a portion of any water and any heavy hydrocarbon that may be present, leaving the olefin and any unreacted alkane or alkyl aromatic primarily in the vapor phase. Olefin and unreacted alkane or alkyl aromatic hydrocarbons can then be removed from the reaction product in one or more separator drums. For example, one or more splitters or distillation columns can be used to separate the dehydrogenated product from the unreacted first hydrocarbon-containing feed.

In some embodiments, a recovered olefin, e.g., propylene, can be used for producing polymer, e.g., recovered propylene can be polymerized to produce polymer having segments or units derived from the recovered propylene such as polypropylene, ethylene-propylene copolymer, etc. Recovered isobutene can be used, e.g., for producing one or more of: an oxygenate such as methyl tert-butyl ether, fuel additives such as diisobutene, synthetic elastomeric polymer such as butyl rubber, etc.

A Second Process for Upgrading a Hydrocarbon

The second process for upgrading a hydrocarbon can include contacting a second hydrocarbon-containing feed with the catalyst composition that includes the catalyst particles that include Pt and optionally the promoter disposed on the support to effect reforming of at least a portion of the second hydrocarbon-containing feed to produce a coked catalyst and an effluent that can include carbon monoxide and molecular hydrogen. The catalyst composition and the second hydrocarbon-containing feed can be contacted with one another within any suitable environment such as one or more reaction or conversion zones disposed within one or more reactors to produce the effluent and the coked catalyst. The reaction or conversion zone can be disposed or otherwise located within one or more fixed bed reactors, one or more fluidized or moving bed reactors, one or more reverse flow reactors, or any combination thereof. For clarity and ease of description, the reforming reaction will be discussed in the context of a fluidized bed reactor, but it should be understood that fixed bed reactors, reverse flow or moving bed reactors, or any other reactor can be used to carry out the reforming of the second hydrocarbon-containing feed.

The reforming reaction can be used to produce reformed hydrocarbons via a continuous reaction process or a discontinuous reaction process. In some embodiments, the reaction process can include a reforming step, e.g., an endothermic reaction, and a regeneration step, e.g., an exothermic reaction, that operate continuously while the fluidized catalyst is transported in-between the reforming and regeneration zone of the reactor. The endothermic reaction can include hydrocarbon reforming in the presence of the catalyst composition. Fresh hydrocarbon and regenerated fluidized catalyst particles can enter the reforming zone. After spending some time in the reforming zone, the hydrocarbon can be at least partially converted to a reforming product that can exit the reforming zone together with the spent catalyst. The reforming product and unreacted feed can be separated from the spent catalyst by one or more separating devices. While the reforming product and unreacted feed from the separating devices go downstream for further purification, the spent catalyst can be sent to the regeneration zone for regeneration. The exothermic regeneration reaction can be the reaction of an oxidant and, optionally a fuel, under combustion conditions to produce a regenerated catalyst and a flue gas. After regeneration, the regenerated catalyst can be separated from the flue gas by one or more separating devices and can be transported back to the reforming zone, joining more hydrocarbon feed to enter the reforming zone to initiate more reforming reaction. The reforming step can convert $CO_2$ and/or $H_2O$ and hydrocarbons, e.g., $CH_4$, to a synthesis gas that includes $H_2$ and CO. The regeneration step can combust reactants, e.g., coke disposed on the spent catalyst and/or the optional fuel and an oxidant, to generate heat that heats up the regenerated catalyst that can provide heat that can be used to drive the reforming reaction. In some embodiments, the catalyst can be heated to an average temperature in a range of from 600° C., 700° C., or 800° C. to 1,000° C., 1,300° C., or 1,600° C. during the regeneration step.

Illustrative fuels can be or can include, but are not limited to, hydrocarbons, e.g., methane, ethane, propane, butane, pentane, or hydrocarbon containing streams, e.g., natural gas, molecular hydrogen, and/or other combustible compounds. The oxidant can be or can include $O_2$. In some embodiments, the oxidant can be or can include air, $O_2$ enriched air, $O_2$ depleted air, or any other suitable $O_2$ containing stream.

The regeneration of the catalyst composition can correspond to removal of coke from the catalyst particles. In some embodiments, during reforming, a portion of the feed introduced into the reforming zone can form coke. This coke can potentially block access to the catalytic sites (such as metal sites) of the catalyst. During regeneration at least a portion of the coke generated during reforming can be removed as CO or $CO_2$. The regeneration of the catalyst composition can also correspond to re-dispersion of any agglomerated active phase of the catalyst such as Pt.

The second hydrocarbon-containing feed can be or can include, but is not limited to, one or more reformable $C_1$-$C_{16}$ hydrocarbons such as alkanes, alkenes, cycloalkanes, alkylaromatics, or any mixture thereof. In some embodiments, the second hydrocarbon-containing stream can be or can include methane, ethane, propane, butane, pentane, or a mixture thereof. In some embodiments, the second hydrocarbon-containing feed can be exposed to the catalyst composition under a pressure of less than 35 kPag. For example, the second hydrocarbon-containing feed can be exposed to the catalyst composition under a pressure in a range of from 0.7 kPag, 2 kPag, 3.5 kPag, 5 kPag, or 10 kPag to 15 kPag, 20 kPag, 25 kPag, or 30 kPag. In other embodiments, the second hydrocarbon-containing feed can be exposed to the catalyst composition under a pressure in a range of from 35 kPag to 15 MPag. In still other embodiments, the second hydrocarbon-containing feed can be exposed to the catalyst under a pressure in a range of from 0.7 kPag, 2 kPag, 5 kPag, 20 kPag, 35 kPag, 50 kPag, or 100 kPag to 200 kPag, 1 MPag, 3 MPag, 5 MPag, 10 MPag, or 15 MPag. In still other embodiments, the second hydrocarbon-containing feed can be exposed to the catalyst under a pressure of less than 2.8 MPag, less than 2.5 MPag, less than 2.2 MPag, or less than 2 MPag.

The reforming reaction of the second hydrocarbon-containing feed, e.g., $CH_4$, can occur in the presence of $H_2O$ (steam-reforming), in the presence of $CO_2$ (dry-reforming), or in the presence of both $H_2O$ and $CO_2$ (bi-reforming). Examples of stoichiometry for steam, dry, and bi-reforming of $CH_4$ are shown in equations (1)-(3).

$$\text{Dry-Reforming: } CH_4 + CO_2 = 2CO + 2H_2 \quad (1)$$

$$\text{Steam-Reforming: } CH_4 + H_2O = CO + 3H_2 \quad (2)$$

$$\text{Bi-Reforming: } 3CH_4 + 2H_2O + CO_2 = 4CO + 8H_2 \quad (3)$$

As shown in equations (1)-(3), dry reforming can produce lower ratios of $H_2$ to CO than steam reforming. Reforming reactions performed with only steam can generally produce a synthesis gas having a $H_2$:CO molar ratio of around 3, such as 2.5 to 3.5. In contrast, reforming reactions performed with only $CO_2$ can generally produce a synthesis gas having a $H_2$:CO molar ratio of roughly 1 or even lower. By using a combination of $CO_2$ and $H_2O$ during reforming, the reforming reaction can be controlled to generate a wide variety of $H_2$ to CO ratios in a resulting synthesis gas.

It should be noted that the ratio of $H_2$ to CO in a synthesis gas can also be dependent on the water gas shift equilibrium. Although the stoichiometry in Equations (1)-(3) shows ratios of roughly 1 or roughly 3 for dry reforming and steam reforming, respectively, the equilibrium amounts of $H_2$ and CO in a synthesis gas can be different from the reaction stoichiometry. The equilibrium amounts can be determined based on the water gas shift equilibrium, which relates the concentrations of $H_2$, CO, $CO_2$ and $H_2O$ based on the reaction shown in equation (4).

$$H_2O + CO \leftrightarrow H_2 + CO_2 \quad (4)$$

In some embodiments, the catalyst composition can also serve as water gas shift catalysts. Thus, if a reaction environment for producing $H_2$ and CO also includes $H_2O$ and/or $CO_2$, the initial stoichiometry from the reforming reaction may be altered based on the water gas shift equilibrium. However, this equilibrium is also temperature dependent, with higher temperatures favoring production of CO and $H_2O$. As a result, the ratio of $H_2$ to CO that is generated when forming synthesis gas is constrained by the water gas shift equilibrium at the temperature in the reaction zone when the synthesis gas is produced.

The ability to adjust the $H_2$:CO molar ratio of the synthesis gas provides a flexible process that can be combined with a wide variety of synthesis gas upgrading processes. Illustrative synthesis gas upgrading processes can include, but are not limited to, Fischer-Tropsch processes, methanol and/or other alcohol synthesis, e.g., one or more $C_1$-$C_4$ alcohols, fermentation processes, separation processes that can separate hydrogen to produce a $H_2$-rich product, dimethyl ether, and combinations thereof. These synthesis gas upgrading processes are well-known to persons having ordinary skill in the art. In some embodiments, the upgraded product can include, but is not limited to, methanol, syncrude, diesel, lubricants, waxes, olefins, dimethyl ether, other chemicals, or any combination thereof.

Systems suitable for carrying out the reforming of the second hydrocarbon-containing feed can include systems that are well-known in the art such as the fixed bed reactors disclosed in WO Publication No. WO2017078894; the fluidized riser reactors and/or downer reactors disclosed in U.S. Pat. Nos. 3,888,762; 7,102,050; 7,195,741; 7,122,160; and 8,653,317; and U.S. Patent Application Publication Nos. 2004/0082824; 2008/0194891; and the reverse flow reactors disclosed in U.S. Pat. Nos. 7,740,829; 8,551,444; 8,754,276; 9,687,803; and 10,160,708; and U.S. Patent Application Publication Nos.: 2015/0065767 and 2017/0137285; and WO Publication No. WO2013169461.

EXAMPLES

The foregoing discussion can be further described with reference to the following non-limiting examples. Catalyst Compositions 1-16 were prepared according to the following procedures.

Catalyst Composition 1: was prepared by mixing CATAPAL© D pseudoboehmite (Sasol) (47 g) and calcined Mg—Al hydrotalcite (PURALOX® MG70) (44 g) that contained 70 wt % MgO and 30 wt % $Al_2O_3$ in deionized water (524 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 50 wt % PURALOX® MG70 and 50 wt % $Al_2O_3$ derived from CATAPAL® D. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 50:50 MG70: CATAPAL® D.

Catalyst Composition 2: was prepared by mixing 40 wt % aluminum chlorohydrol solution (ACH) (85 g) and calcined Mg—Al hydrotalcite (PURALOX® MG70) (88 g) in deionized water (596 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 80 wt % PURALOX® MG70 and 20 wt % $Al_2O_3$ derived from ACH. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 80:20 MG70:ACH.

Catalyst Composition 3: was prepared by mixing 40 wt % aluminum chlorohydrol solution (ACH) (3,191 g) and calcined Mg—Al hydrotalcite (PURALOX® MG70) (1,923 g) in deionized water (11,500 g) to prepare a slurry. The slurry was milled and spray dried using a Bowen laboratory spray dryer (Bowen Engineering, Inc., BE-1436) to produce spray dried particles. The spray dried particles were calcined in air at 550° C. for 4 hours to produce calcined support particles containing nominally 70 wt % PURALOX® MG70 and 30 wt % $Al_2O_3$ derived from ACH. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 70:30 MG70:ACH.

Catalyst Composition 4: was prepared by mixing 40 wt % aluminum chlorohydrol solution (ACH) (43 g), CATAPAL® D pseudoboehmite (12 g), and calcined Mg—Al hydrotalcite (PURALOX® MG70) (88 g) in deionized water (596 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 80 wt % PURALOX® MG70, 10 wt % $Al_2O_3$ derived from ACH, and 10 wt % $Al_2O_3$ derived from CATAPAL® D. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 80:10:10 MG70:ACH:CATAPAL® D.

Catalyst Composition 5: was prepared by mixing 40 wt % aluminum chlorohydrol solution (ACH) (42 g), calcined Mg—Al hydrotalcite (PURALOX® MG70) (97 g), and tin (II) chloride dihydrate (3 g) in deionized water (600 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 90 wt % PURALOX® MG70 and 10 wt % $Al_2O_3$ derived from ACH. The calcined support particles were impregnated with an aqueous solution that included chloroplatinic acid hexahydrate and deionized water using incipient wetness impregnation. The impregnated material was calcined in air at 800° C. for 12 hours to produce the catalyst composition containing nominally 0.3 wt % Pt and 1.5 wt % Sn on 90:10 MG70:ACH.

Catalyst Composition 6: was prepared by mixing 40 wt % aluminum chlorohydrol solution (ACH) (42 g), calcined Mg—Al hydrotalcite (PURALOX® MG70) (97 g), tin (II) chloride dehydrate (3 g), and 3.1 wt % tetraammineplatinum (II) nitrate solution (10 g) in deionized water (592 ml) to prepare a slurry. The slurry was milled and spray dried on a Buchi B-290 Mini Spray Dryer to produce spray dried particles. The spray dried particles were calcined in air at 800° C. for 12 hours to produce the catalyst composition containing nominally 0.3 wt % Pt and 1.5 wt % Sn on 90:10 MG70:ACH.

Catalyst Composition 7: was prepared by mixing 40 wt % aluminum chlorohydrol solution (ACH) (85 g) and MgO (Sigma-Aldrich) (85 g) in deionized water (599 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 80 wt % MgO and 20 wt % $Al_2O_3$ derived from ACH. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 80:20 MgO:ACH.

Catalyst Composition 8: was prepared by mixing 10 nm MgO (US Research Nanomaterials) (42 g) and acetic acid (10 g) in deionized water (162 ml). In a separate mixture, DISPERAL® P2 pseudoboehmite (Sasol) (42 g) was added to deionized water (354 ml). The DISPERAL® P2 mixture was added to the MgO mixture to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 50 wt % MgO and 50 wt % $Al_2O_3$ derived from DISPERAL® P2.

Catalyst Composition 9: was prepared by mixing calcined Mg—Al hydrotalcite (PURALOX® MG70) (33 g) and acetic acid (10 g) in deionized water (171 ml). In a separate mixture, DISPERAL® P2 pseudoboehmite (42 g) (Sasol) was added to deionized water (354 ml). The DISPERAL® P2 mixture was added to the MG70 mixture to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 50 wt % PURALOX® MG70 and 50 wt % $Al_2O_3$ derived from DISPERAL® P2.

Catalyst Composition 10: was prepared by mixing 40 wt % colloidal $SiO_2$ (LUDOX® AS-40) (50 g) and calcined Mg—Al hydrotalcite (PURALOX® MG70) (22 g) in deionized water (236 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 50 wt % PURALOX® MG70 and 50 wt % $SiO_2$ derived from LUDOX® AS-40. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 50:50 MG70:AS-40 $SiO_2$.

Catalyst Composition 11: was prepared by mixing Kaolin clay (Natka) (23 g) and calcined Mg—Al hydrotalcite (PURALOX® MG70) (22 g) in deionized water (263 ml) to prepare a slurry. The slurry was milled and spray dried on a Buchi B-290 Mini Spray Dryer to produce spray dried particles. The spray dried particles were calcined in air at 550° C. for 4 hours to produce calcined support particles containing nominally 50 wt % PURALOX® MG70 and 50 wt % Kaolin clay (Natka). The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on 50:50 MG70: Natka clay.

Catalyst Composition 12: was prepared by mixing $Mg(NO_3)_2 \cdot 6H_2O$ (26.16 g) and $Al(NO_3)_3 \cdot 9H_2O$ (18.81 g) in deionized water (100 ml) followed by dropwise addition of 25 wt % $NH_4OH$ (51.08 g) yielding a gel. The above gel was centrifuged for 30 min (3500 rpm) in order to remove the supernatant from the gel. The re-dispersed gel in water (100 ml) was spray-dried on a Buchi B-290 Mini Spray Dryer to produce spray-dried particles. The spray-dried particles were calcined in air at 550° C. for 4 hours to produce calcined support particles containing nominally 62 wt % MgO and 38 wt % $Al_2O_3$. The calcined support has a BET surface area of 194 $m^2/g$ and an apparent loose bulk density of 1.05 g/mL. The calcined support particles were impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on the calcined support.

Catalyst Composition 13: A commercial spray-dried, calcined hydrotalcite sample containing 73.4 wt % MgO, 22.7 wt % $Al_2O_3$ was obtained from HCPECT (HyBA-1). The sample has an apparent bulk density of 0.8 g/ml and an attrition loss after one hour of 0.35 wt % (ASTM D5757-11(2017)). The sample was impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on HyBA-1.

Catalyst Composition 14: A commercial spray-dried, calcined hydrotalcite sample containing 54.4 wt % MgO, 44.6 wt % $Al_2O_3$ was obtained from HCPECT (HT-MA150). The sample has a median particle size of 80 μm, and an attrition loss after one hour and apparent bulk density meeting FCC additive requirements. The sample was impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on HT-MA150.

Catalyst Composition 15: A commercial spray-dried, calcined hydrotalcite sample containing 66.3 wt % MgO, 30.7 wt % $Al_2O_3$ was obtained from HOUDRY (DP2022). The sample has an average particle size of 79.6 μm, an apparent bulk density of 0.81 g/ml, and an attrition loss after one hour of 1.6 wt % (ASTM D5757-11(2017)) (RIPP). The sample was impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on DP2022.

Catalyst Composition 16: To increase the amount of hydrotalcite, 6 g DP2022 was hot-rolled with 48 ml of DI water in an autoclave at 145° C. for 5 days. The solid product was recovered and dried at 80° C. for 3 hours. X-ray Diffraction (XRD) shows that the product is hydrotalcite with a high phase purity. The product was calcined in air at 550° C. for 3 h. It was then impregnated with an aqueous solution that included tin (IV) chloride pentahydrate, chloroplatinic acid hexahydrate, and deionized water using incipient wetness impregnation. The impregnated material was calcined in air at 800° C. for 12 hours to produce the catalyst composition containing nominally 0.3 wt % Pt and 1.5 wt % Sn on the support.

Properties of the supports for catalyst compositions 1-11 are shown in Table 1 below.

TABLE 1

| Support | Support Composition | Apparent Loose Bulk Density (g/cm$^3$) | Median Particle Size (μm) |
|---|---|---|---|
| 1 | 50:50 MG70:CATAPAL ® D | 0.45 | 19.7 |
| 2 | 80:20 MG70:ACH | 0.51 | 26.9 |
| 3 | 70:30 MG70:ACH | 0.43 | 54 |
| 4 | 80:10:10 MG70:ACH:CATAPAL ® D | 0.39 | 25.4 |
| 5 | 90:10 MG70:ACH | 0.31 | 28 |
| 6 | 90:10 MG70:ACH | 0.38 | 31.5 |
| 7 | 80:20 MgO:ACH | 0.59 | 21.4 |
| 8 | 50:50 MgO:DISPERAL ® P2 | 0.57 | 24 |
| 9 | 50:50 MG70:DISPERAL ®P2 | 0.68 | 19 |
| 10 | 50:50 MG70:AS-40 $SiO_2$ | — | 10 |
| 11 | 50:50 MG70:Natka clay | — | 22.6 |

Examples Using the Catalysts Described Above

Fixed bed experiments were conducted at approximately 100 kPa-absolute that used the catalyst compositions 1-6 and 13-16 (Example 1-6 and Examples 13-16, respectively). A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of catalyst was mixed with an appropriate amount of quartz diluent and loaded into a quartz reactor. The amount of diluent was determined so that the catalyst bed (catalyst+diluent) overlaps with the isothermal zone of the quartz reactor and the catalyst bed is largely isothermal during operation. The dead volume of the reactor was filled with quartz chips/rods.

The concentration of each component in the reactor effluent was used to calculate the $C_3H_6$ yield and selectivity. The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in the table below.

The process steps for Examples 1-6 and 13-16 were as follows: 1. The system was flushed with an inert gas. 2. An oxygen containing gas with 90 vol % dry air and 10 vol % steam at a flow rate of 93.2 sccm was passed through a by-pass of the reaction zone, while an inert was passed through the reaction zone. The reaction zone was heated to a regeneration temperature of 800° C. 3. The oxygen containing gas with 90 vol % air and 10 vol % steam was then passed through the reaction zone for 1 min to regenerate the catalyst. This is followed by flowing 83.9 sccm of dry air through the reaction zone for an additional 10 min. 4. The system was flushed with an inert gas. 5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 s. 6. The system was flushed with an inert gas. During this process, the temperature of the reaction zone was changed from 800° C. to a reaction temperature of 655° C. 7. A hydrocarbon-containing (HCgas) feed that included 81 vol % of $C_3H_8$, 9 vol % of inert gas (Ar or Kr) and 10 vol % of steam at a flow rate of 17.6 sccm was passed through the by-pass of the reaction zone for a certain period of time, while an inert gas was passed through the reaction zone. The hydrocarbon-containing feed was then passed through the reaction zone at 655° C. for 10 min. GC sampling of the reaction effluent started as soon as the feed was switched from the by-pass of the reaction zone to the reaction zone.

The above process steps were repeated in cycles until stable performance was obtained. Table 2 shows that Catalyst 1-6 were active and selective for propane dehydrogenation. FIG. 1 shows that Catalyst 2 was stable over 60 cycles for propane dehydrogenation. Table 3 shows that Catalysts 13-16 were active and selective for propane dehydrogenation. In FIG. 1, the vertical axis shows the selectivities, and the horizontal axis shows time on stream in hours.

TABLE 2

| Example | | 1 | 2 | 3 | 4 | 5 | 6 |
|---|---|---|---|---|---|---|---|
| Performance | $Y_{ini}$ | 59.4 | 62.9 | 60.3 | 62.9 | 63.6 | 63.5 |
| | $Y_{end}$ | 52.4 | 59.2 | 58.3 | 59.7 | 61.1 | 61 |
| | $S_{ini}$ | 95.3 | 94.4 | 91.5 | 94.5 | 95.1 | 94.1 |
| | $S_{end}$ | 96.3 | 95.9 | 94.4 | 96.1 | 96.3 | 95.7 |

TABLE 3

| Example | | 13 | 14 | 15 | 16 |
|---|---|---|---|---|---|
| Performance | $Y_{ini}$ | 58.5 | 56.4 | 43.7 | 56.1 |
| | $Y_{end}$ | 56.5 | 46 | 33.8 | 49.3 |
| | $S_{ini}$ | 94 | 93 | 86.6 | 89.2 |
| | $S_{end}$ | 96.3 | 95.5 | 92.2 | 94.3 |

Catalyst Compositions 17-30 were prepared according to the following procedures. For each catalyst composition PURALOX® MG 80/150 (3 grams) (Sasol), which was a mixed Mg/Al metal oxide that contained 80 wt % of MgO and 20 wt % of $Al_2O_3$ and had a surface area of 150 $m^2/g$, was calcined under air at 550° C. for 3 hours to form a support. Solutions that contained a proper amount of tin (IV) chloride pentahydrate when used to make the catalyst composition (Acros Organics) and/or chloroplatinic acid when used to make the catalyst composition (Sigma Aldrich), and 1.8 ml of deionized water were prepared in small glass vials. The calcined PURALOX® MG 80/150 supports (2.3 grams) for each catalyst composition were impregnated with the corresponding solution. The impregnated materials were allowed to equilibrate in a closed container at room temperature (RT) for 24 hours, dried at 110° C. for 6 hours, and calcined at 800° C. for 12 hours. Table 4 shows the nominal Pt and Sn content of each catalyst composition based on the weight of the support.

TABLE 4

| Catalyst | Pt (wt %) | Sn (wt %) |
|---|---|---|
| 17 | 0.4 | 1 |
| 18 | 0.3 | 1 |
| 19 | 0.2 | 1 |
| 20 | 0.1 | 1 |
| 21 | 0.05 | 1 |
| 22 | 0.025 | 1 |
| 23 | 0.0125 | 1 |
| 24 | 0 | 1 |
| 25 | 0.1 | 0.5 |
| 26 | 0.1 | 1 |
| 27 | 0.1 | 2 |

TABLE 4-continued

| Catalyst | Pt (wt %) | Sn (wt %) |
|---|---|---|
| 28 | 0.0125 | 0 |
| 29 | 0.0125 | 0.5 |
| 30 | 0.0125 | 2 |

Examples Using the Catalyst Compositions of Examples 17-30

Fixed bed experiments were conducted at approximately 100 kPa-absolute that used catalysts 17-24. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of the catalyst composition was mixed with an appropriate amount of quartz diluent and loaded into a quartz reactor. The amount of diluent was determined so that the catalyst bed (catalyst+diluent) overlapped with the isothermal zone of the quartz reactor and the catalyst bed was largely isothermal during operation. The dead volume of the reactor was filled with quartz chips/rods.

The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in Tables 5 and 6 below for catalysts 17-24.

The process steps for catalysts 17-24 were as follows: 1. The system was flushed with an inert gas. 2. Dry air at a flow rate of 83.9 sccm was passed through a by-pass of the reaction zone, while an inert was passed through the reaction zone. The reaction zone was heated to a regeneration temperature of 800° C. 3. Dry air at a flow rate of 83.9 sccm was then passed through the reaction zone for 10 min to regenerate the catalyst. 4. The system was flushed with an inert gas. 5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 seconds. 6. The system was flushed with an inert gas. During this process, the temperature of the reaction zone was changed from 800° C. to a reaction temperature of 670° C. 7. A hydrocarbon-containing (HCgas) feed that included 81 vol % of $C_3H_8$, 9 vol % of inert gas (Ar or Kr) and 10 vol % of steam at a flow rate of 35.2 sccm was passed through the by-pass of the reaction zone for a certain period of time, while an inert gas was passed through the reaction zone. The hydrocarbon-containing feed was then passed through the reaction zone at 670° C. for 10 min. GC sampling of the reaction effluent started as soon as the feed was switched from the by-pass of the reaction zone to the reaction zone.

The above process steps were repeated in cycles until stable performance was obtained. Tables 5 and 6 show that Catalyst 22 that contained only 0.025 wt % of Pt and 1 wt % of Sn had both a similar yield and a similar selectivity as compared to Catalyst 17 that contained 0.4 wt % of Pt and 1 wt % of Sn, which was surprising and unexpected. Catalyst 24 that did not include any Pt did not show an appreciable propylene yield.

TABLE 5

| | | Catalyst 17 | Catalyst 18 | Catalyst 19 | Catalyst 20 |
|---|---|---|---|---|---|
| Performance | $Y_{ini}$ | 61.7 | 61.7 | 60.7 | 63.7 |
| | $Y_{end}$ | 55.2 | 55.7 | 54.2 | 56.7 |
| | $S_{ini}$ | 97.3 | 97.2 | 97.0 | 97.1 |
| | $S_{end}$ | 98.1 | 98.0 | 97.7 | 98.3 |

TABLE 6

| | | Catalyst 21 | Catalyst 22 | Catalyst 23 | Catalyst 24 |
|---|---|---|---|---|---|
| Performance | $Y_{ini}$ | 62.4 | 62.0 | 56.7 | 2.0 |
| | $Y_{end}$ | 57.2 | 54.6 | 45.7 | 1.7 |
| | $S_{ini}$ | 96.7 | 97.3 | 96.9 | 64.2 |
| | $S_{end}$ | 97.7 | 98.0 | 97.6 | 49.5 |

Catalyst compositions 25-30 were also tested using the same process steps 1-7 described above with regard to catalysts 17-24. Table 7 shows that the level of Sn should not be too low or too high for optimal propylene yield for the catalyst compositions that included 0.1 wt % of Pt based on the weight of the support.

TABLE 7

| | | Catalyst 25 0.5 wt % Sn | Catalyst 20 1 wt % Sn | Catalyst 26 1 wt % Sn | Catalyst 27 2 wt % Sn |
|---|---|---|---|---|---|
| Performance | $Y_{ini}$ | 58.4 | 63.7 | 63.4 | 56.5 |
| | $Y_{end}$ | 49.5 | 56.7 | 55.5 | 47.7 |
| | $S_{ini}$ | 96.9 | 97.1 | 97.2 | 97.8 |
| | $S_{end}$ | 97.6 | 98.3 | 98.1 | 98.2 |

Table 8 shows that the level of Sn should not be too high or too low for optimal propylene yield for the catalyst compositions that included 0.0125 wt % of Pt based on the weight of the support.

TABLE 8

| | | Catalyst 28 0 wt % Sn | Catalyst 29 0.5 wt % Sn | Catalyst 23 1 wt % Sn | Catalyst 30 2 wt % Sn |
|---|---|---|---|---|---|
| Performance | $Y_{ini}$ | 2.6 | 44 | 56.7 | 55.4 |
| | $Y_{end}$ | 1.7 | 24.4 | 45.7 | 44.1 |
| | $S_{ini}$ | 63.9 | 96.7 | 96.9 | 96.8 |
| | $S_{end}$ | 61.1 | 95.6 | 97.6 | 97.6 |

Figure 2:
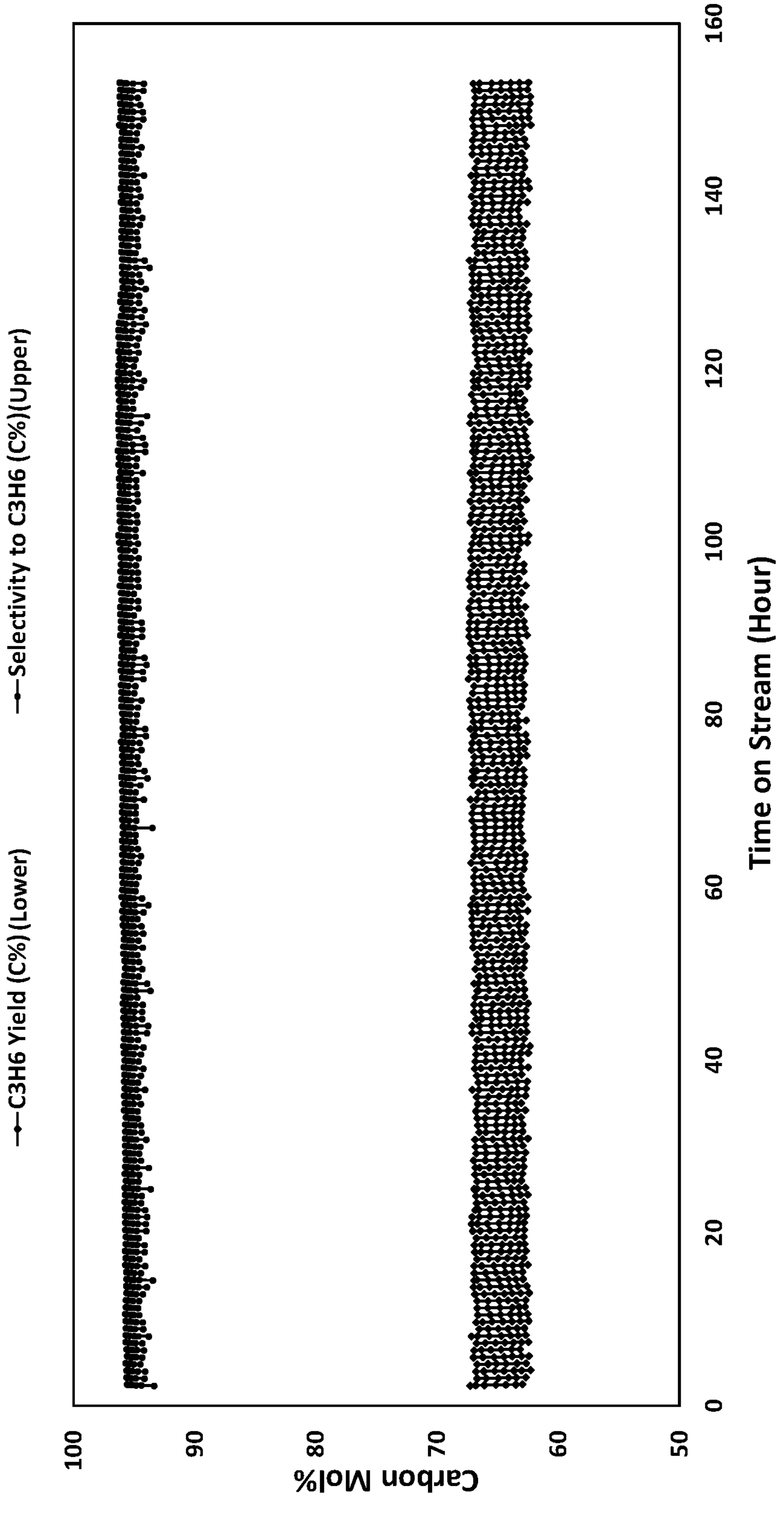
FIG. 2 shows a catalyst composition (catalyst 22) maintained its performance for 204 cycles.

Catalyst composition 22 that contained only 0.025 wt % of Pt and 1 wt % of Sn was also subjected to a longevity test using the same process steps 1-7 described above with regard to catalysts 17 to 24, except a flow rate of 17.6 sccm was used instead of 35.2 sccm in step 7. FIG. 2 shows that catalyst composition 22 maintained performance for 204 cycles (x-axis is time, y-axis is $C_3H_6$ yield and selectivity to $C_3H_6$, both in carbon mole %).

Listing of Embodiments

This disclosure may further include the following non-limiting embodiments.

A1. A process for upgrading a hydrocarbon, comprising: (I) contacting a hydrocarbon-containing feed with catalyst particles comprising Pt disposed on a support to effect reforming of at least a portion of the hydrocarbon-containing feed to produce a coked catalyst and a synthesis gas comprising $H_2$ and CO, wherein: the hydrocarbon-containing feed comprises one or more $C_1$-$C_{16}$ hydrocarbons and $H_2O$, $CO_2$, or a mixture of $H_2O$ and $CO_2$, the hydrocarbon-containing feed and catalyst are contacted at a temperature of 400° C. or more, the support comprises at least 0.5 wt % of a Group 2 element, the catalyst comprises from 0.001 wt % to 6 wt % of the Pt based on the weight of the support, the catalyst particles have a median particle size in a range of from 10 μm to 500 μm, and the catalyst particles have an apparent loose bulk density in a range of from 0.3 g/cm$^3$ to 2 g/cm$^3$ as measured according to ASTM D7481-18 modified with a 10, 25, or 50 mL graduated cylinder instead of a 100 or 250 mL graduated cylinder.

A2. The process of A1, further comprising (II) contacting at least a portion of the coked catalyst with an oxidant to effect combustion of at least a portion of the coke to produce a regenerated catalyst lean in coke and a combustion gas.

A3. The process of A2, further comprising (III) contacting a fuel with the oxidant and the catalyst to effect combustion of at least a portion of the fuel.

A4. The process of A2 or A3, further comprising (IV) contacting an additional quantity of the hydrocarbon-containing feed with at least a portion of the regenerated catalyst to produce a re-coked catalyst and additional effluent.

A5. The process of any of A1 to A4, wherein the hydrocarbon-containing feed is contacted with the catalyst particles in a fluidized bed reactor.

A6. The process of any of A1 to A4, wherein the hydrocarbon-containing feed is contacted with the catalyst particles in a fixed bed reactor.

A7. The process of any of A1 to A4, wherein the hydrocarbon-containing feed is contacted with the catalyst particles in a reverse flow reactor.

A8. The process of any of A1 to A7, wherein the catalyst particles further comprise up to 10 wt % of a promoter comprising Sn, Cu, Au, Ag, Ga, or a combination thereof, or a mixture thereof disposed on the support.

A9. The process of any of A1 to A8, wherein the catalyst particles further comprise an alkali metal element comprising Li, Na, K, Rb, Cs, or a combination thereof, or a mixture thereof disposed on the support in an amount of up to 5 wt % based on the weight of the support.

A10. The process of any of A1 to A9, wherein the catalyst particles have a size and particle density that is consistent with a Geldart A or Geldart B definition of a fluidizable solid.

A11. The process of any of A1 to A10, wherein the support further comprises a binder in a range of from 5 wt % to 90 wt % based on the weight of the support.

A12. The process of any of A1 to A11, wherein: the Group 2 element comprises Mg, and at least a portion of the Group 2 element is in the form of MgO or a mixed oxide comprising MgO.

A13. The process of any of A1 to A11, wherein: the Group 2 element comprises Mg, and at least a portion of the Group 2 element is in the form of a mixed Mg/Al oxide.

A14. The process of any of A1 to A13, further comprising at least one of: reacting at least a portion of the synthesis gas under effective Fischer-Tropsch conditions in the presence of a Fischer-Tropsch catalyst to produce an upgraded product, wherein the Fischer-Tropsch catalyst comprises a shifting Fischer-Tropsch catalyst or a non-shifting Fischer-Tropsch catalyst; subjecting at least a portion of the synthesis gas to a fermentation process to produce an alcohol, an organic acid, or a mixture thereof; contacting at least a portion of the synthesis gas with a catalyst to produce at least one $C_1$-$C_4$ alcohol; and separating $H_2$ from the synthesis gas to produce a $H_2$-rich product.

B1. A process for making a catalyst composition, comprising: (I) preparing a slurry or gel comprising a compound containing a Group 2 element and a liquid medium; and (II) spray drying the slurry or the gel to produce spray dried support particles comprising the Group 2 element, wherein, at least one of (i) and (ii) is met: (i) Pt is present in the slurry or the gel in the form of a Pt-containing compound and the catalyst composition comprises catalyst particles comprising the spray dried support particles having Pt disposed thereon, and (ii) Pt is deposited on the spray dried support particles by contacting the spray dried particles with a Pt-containing compound to produce Pt-containing spray dried support particles and the catalyst composition comprises catalyst particles comprising the spray dried support particles having Pt disposed thereon, and wherein, at least one of (iii) and (iv) is met: (iii) a compound comprising a promoter element is present in the slurry or the gel and the catalyst composition comprises catalyst particles comprising the spray dried support particles having the promoter element disposed thereon, and (iv) a compound comprising a promoter element is deposited on the spray dried support particles to produce promoter-containing spray dried support particles and the catalyst composition comprises catalyst particles comprising the spray dried support particles having the promoter element disposed thereon, wherein: the promoter element comprises Sn, Cu, Au, Ag, Ga, or a combination thereof, or a mixture thereof, the catalyst particles comprise from 0.001 wt % to 6 wt % of the Pt based on the weight of the spray dried support particles, the catalyst particles comprise at least 0.5 wt % of the Group 2 element based on the weight of the spray dried support particles, the catalyst particles have a median particle size in a range of from 10 μm to 500 μm, and the catalyst particles have an apparent loose bulk density in a range of from 0.3 g/cm$^3$ to 2 g/cm$^3$ as measured according to ASTM D7481-18 modified with a 10, 25, or 50 mL graduated cylinder instead of a 100 or 250 mL graduated cylinder.

B2. The process of B1, wherein the Pt-containing compound is present in the slurry or the gel.

B3. The process of B1 or B2, wherein the Pt-containing compound is deposited on the spray dried support particles.

B4. The process of any of B1 to B3, wherein the compound comprising the promoter elements is present in the slurry or the gel.

B5. The process of any of B1 to B4, wherein the compound comprising the promoter is deposited on the spray dried support particles.

B6. The process of any of B1 to B5, wherein: the slurry or gel prepared in step (I) further comprises a binder, a binder precursor, or a mixture thereof.

B7. The process of any of B1 to B6, wherein: the Group 2 element comprises Mg, and at least a portion of the Group 2 element in the spray dried support particles is in the form of a mixed Mg/Al oxide.

B8. The process of any of B1 to B7, further comprising: (III) calcining the spray dried support particles under an oxidative atmosphere to produce calcined support particles, wherein the catalyst composition comprises catalyst particles comprising the calcined support particles comprising the Group 2 element and having Pt and the promoter element disposed thereon.

B9. The process of B8, further comprising: (IV) hydrating the calcined support particles after step (III) to produce hydrated support particles; and (V) calcining the hydrated support particles to produce the catalyst composition comprising re-calcined support particles, wherein the catalyst particles produced via steps (IV) and (V) have an attrition loss after one hour that is less than an attrition loss after one hour of the calcined particles produced in step (III), as measured according to ASTM D5757-11(2017).

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A catalyst composition comprising catalyst particles, wherein the catalyst particles comprise 0.001 wt % to 6 wt % of Pt and up to 10 wt % of a promoter comprising Sn, Cu, Au, Ag, Ga, or a combination thereof, or a mixture thereof disposed on a support, the support comprising at least 0.5 wt % of a Group 2 element, wherein all weight percent values are based on the weight of the support, and the catalyst particles have a median particle size in a range from 10 μm to 500 μm, and an apparent loose bulk density in a range from 0.3 g/cm$^3$ to 2 g/cm$^3$, as measured according to ASTM D7481-18 modified with a 10, 25, or 50 mL graduated cylinder instead of a 100 or 250 mL graduated cylinder.

2. The catalyst composition of claim 1, wherein the catalyst particles have an attrition loss after one hour of ≤5, as measured according to ASTM D5757-11 (2017).

3. The catalyst composition of claim 1, wherein the promoter comprises Sn.

4. The catalyst composition of claim 1, further comprising an alkali metal element comprising Li, Na, K, Rb, Cs, or a combination thereof, or a mixture thereof disposed on the support in an amount of up to 5 wt % based on the weight of the support.

5. The catalyst composition of claim 1, wherein the catalyst particles have a size and particle density that is consistent with a Geldart A or Geldart B definition of a fluidizable solid.

6. The catalyst composition of claim 1, wherein the support further comprises a binder in a range of from 5 wt % to 90 wt % based on the weight of the support.

7. The catalyst composition of claim 6, wherein the binder comprises alumina, silica, zirconia, titania, Kaolin clay, silicon carbide, or a combination thereof, or a mixture thereof.

8. The catalyst composition of claim 1, wherein:

the Group 2 element comprises Mg, and at least a portion of the Group 2 element is in the form of MgO or a mixed oxide comprising MgO.

9. The catalyst composition of claim 1, wherein:
the Group 2 element comprises Mg, and
at least a portion of the Group 2 element is in the form of a mixed Mg/Al oxide.

10. A process for making a catalyst composition of claim 1 comprising catalyst particles, the process comprising:
(I) preparing a slurry or gel comprising a compound containing a Group 2 element and a liquid medium;
(II) spray drying the slurry or the gel to produce spray dried particles comprising the Group 2 element; and
(III) calcining the spray dried particles under an oxidative atmosphere to produce calcined support particles comprising the Group 2 element,
wherein, at least one of (i), (ii), and (iii) is met:
(i) Pt is present in the slurry or the gel in the form of a Pt-containing compound and the catalyst composition comprises catalyst particles comprising the calcined support particles having Pt disposed thereon,
(ii) Pt is deposited on the spray dried particles by contacting the spray dried particles with a Pt-containing compound to produce Pt-containing spray dried particles and the catalyst composition comprises catalyst particles comprising the calcined support particles having Pt disposed thereon, and
(iii) Pt is deposited on the calcined support particles by contacting the calcined support particles with a Pt-containing compound to produce Pt-containing calcined support particles, and the process further comprises (IV) calcining the Pt-containing calcined support particles to produce re-calcined support particles having Pt disposed thereon, wherein the catalyst composition comprises catalyst particles comprising the re-calcined support particles, and wherein, at least one of (iv), (v), and (vi) is met:
(iv) a compound comprising a promoter is present in the slurry or the gel and the catalyst composition comprises catalyst particles comprising the calcined support particles having the promoter disposed thereon,
(v) a compound comprising a promoter is deposited on the spray dried particles to produce promoter-containing spray dried particles and the catalyst composition comprises catalyst particles comprising the calcined support particles having the promoter disposed thereon, and
(vi) a compound comprising a promoter is deposited on the calcined support particles to produce promoter-containing calcined support particles, and the process further comprises (V) calcining the promoter-containing calcined support particles to produce re-calcined support particles having the promoter disposed thereon, wherein the catalyst composition comprises catalyst particles comprising the re-calcined support particles, wherein:
the promoter comprises Sn, Cu, Au, Ag, Ga, or a combination thereof, or a mixture thereof,
the catalyst particles comprise 0.001 wt % to 6 wt % of the Pt and up to 10 wt % of the promoter disposed on the calcined support particles and/or the re-calcined support particles,
the calcined support particles and/or the re-calcined support particles comprise at least 0.5 wt % of the Group 2 element,
all weight percent values are based on the weight of the calcined support particles and/or the re-calcined support particles,
the catalyst particles have a median particle size in a range of from 10 μm to 500 μm, and
the catalyst particles have an apparent loose bulk density in a range of from 0.3 g/cm$^3$ to 2 g/cm$^3$ as measured according to ASTM D7481-18 modified with a 10, 25, or 50 mL graduated cylinder instead of a 100 or 250 mL graduated cylinder.

11. The process of claim 10, wherein the spray dried particles are calcined at a temperature in a range of from 550° C. to 900° C. for a time period of ≤45 minutes.

12. The process of claim 10, wherein the spray dried particles are calcined at a temperature of ≤550° C. for a time period of ≤45 minutes.

13. The process of claim 10, wherein the Pt-containing compound is present in the slurry or the gel.

14. The process of claim 10, wherein the Pt-containing compound is deposited on the spray dried particles.

15. The process of claim 10, wherein the Pt-containing compound is deposited on the calcined support particles and the process further comprises step (IV).

16. The process of claim 10, wherein the compound comprising the promoter is present in the slurry or the gel.

17. The process of claim 10, wherein the compound comprising the promoter is deposited on the spray dried particles.

18. The process of claim 10, wherein the compound comprising the promoter is deposited on the calcined support particles and the process further comprises step (V).

19. The process of claim 10, further comprising:
(VI) hydrating the calcined support particles after step (III) to produce hydrated support particles; and
(VII) calcining the hydrated support particles to produce the catalyst composition comprising re-calcined support particles, wherein the catalyst particles produced via steps (VI) and (VII) have an attrition loss after one hour that is less than an attrition loss after one hour of the calcined particles produced in step (III), as measured according to ASTM D5757-11 (2017).

20. The process of claim 10, wherein: the slurry or gel prepared in step (I) further comprises a binder, a binder precursor, or a mixture thereof.

21. The process of claim 10, wherein:
the Group 2 element comprises Mg, and
at least a portion of the Group 2 element in the calcined support particles or the re calcined support particles is in the form of a mixed Mg/Al oxide.

22. A process for upgrading a hydrocarbon with the catalyst of claim 1 comprising:
(I) contacting a hydrocarbon-containing feed with catalyst particles comprising Pt and a promoter disposed on a support to effect one or more of dehydrogenation, dehydroaromatization, and dehydrocyclization of at least a portion of the hydrocarbon-containing feed to produce a coked catalyst and an effluent comprising one or more upgraded hydrocarbons and molecular hydrogen, wherein:
the hydrocarbon-containing feed comprises one or more of $C_2$-$C_{16}$ linear or branched alkanes, or one or more of $C_4$-$C_{16}$ cyclic alkanes, or one or more $C_8$-$C_{16}$ alkyl aromatics, or a mixture thereof,
the hydrocarbon-containing feed and catalyst are contacted at a temperature in a range of from 300° C. to 900° C., for a time period of ≤3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatics in the hydrocarbon-containing feed, the support comprises at least 0.5 wt % of a Group 2 element, the catalyst particles comprise 0.001 wt % to 6 wt % of the Pt and up to 10 wt % of the promoter disposed on the support, the promoter comprises Sn, Cu, Au, Ag, Ga, or a combination thereof, or a mixture thereof, all weight percent values are based on the weight of the support, the catalyst particles have a median particle size in a range of from 10 μm to 500 μm, the catalyst particles have an apparent loose bulk density in a range of from 0.3 $g/cm^3$ to 2 $g/cm^3$, as measured according to ASTM D7481-18 modified with a 10, 25, or 50 mL graduated cylinder instead of a 100 or 250 mL graduated cylinder, and the one or more upgraded hydrocarbons comprise at least one of a dehydrogenated hydrocarbon, a dehydroaromatized hydrocarbon, and a dehydrocyclized hydrocarbon.

23. The process of claim 22, further comprising:

(II) contacting at least a portion of the coked catalyst with an oxidant to effect combustion of at least a portion of the coke to produce a regenerated catalyst lean in coke and a combustion gas; and (III) contacting an additional quantity of the hydrocarbon-containing feed with at least a portion of the regenerated catalyst to produce a re-coked catalyst and additional effluent, wherein a cycle time from contacting the hydrocarbon-containing feed with the catalyst particles in step (I) to contacting the additional quantity of the hydrocarbon-containing feed with the regenerated catalyst in step (III) is ≤5 hours.

24. The process of claim 22, wherein the promoter comprises Sn.

* * * * *